United States Patent
Engell et al.

(10) Patent No.: US 9,523,778 B2
(45) Date of Patent: Dec. 20, 2016

(54) CALIBRATION AND NORMALIZATION SYSTEMS AND METHODS FOR RADIOPHARMACEUTICAL SYNTHESIZERS

(71) Applicant: GE HEALTHCARE LIMITED, Little Chalfont (GB)

(72) Inventors: Torgrim Engell, Oslo (NO); Julian Grigg, Amersham (GB)

(73) Assignee: GE HEALTHCARE LIMITED

( * ) Notice: Subject to any disclaimer, the term of this patent is extended or adjusted under 35 U.S.C. 154(b) by 185 days.

(21) Appl. No.: 14/348,189

(22) PCT Filed: Sep. 28, 2012

(86) PCT No.: PCT/US2012/057930
§ 371 (c)(1),
(2) Date: Mar. 28, 2014

(87) PCT Pub. No.: WO2013/049577
PCT Pub. Date: Apr. 4, 2013

(65) Prior Publication Data
US 2014/0243500 A1 Aug. 28, 2014

Related U.S. Application Data

(60) Provisional application No. 61/541,246, filed on Sep. 30, 2011.

(51) Int. Cl.
| | | |
|---|---|---|
| *G01N 33/46* | (2006.01) | |
| *G01N 33/50* | (2006.01) | |
| *G01T 7/00* | (2006.01) | |
| *C07B 59/00* | (2006.01) | |
| *G06F 19/12* | (2011.01) | |

(52) U.S. Cl.
CPC .............. *G01T 7/005* (2013.01); *C07B 59/00* (2013.01); *C07B 59/008* (2013.01); *G06F 19/12* (2013.01)

(58) Field of Classification Search
None
See application file for complete search history.

(56) References Cited

U.S. PATENT DOCUMENTS

| | | | |
|---|---|---|---|
| 2007/0040115 A1* | 2/2007 | Publicover et al. | 250/305 |
| 2009/0005617 A1 | 1/2009 | Maeding et al. | |
| 2011/0070161 A1* | 3/2011 | Achanath et al. | 424/1.89 |

FOREIGN PATENT DOCUMENTS

| | | |
|---|---|---|
| WO | WO 2004/100490 | 11/2004 |
| WO | 2009/149367 A1 | 12/2009 |
| WO | 2010/065810 A2 | 6/2010 |

OTHER PUBLICATIONS

Pettitt et al. The development of an automated synthesis of an RGD peptide [18F] fluciclatide utilising chemometric design. Journal of Nuclear Medicine, May 2010, vol. 51, supplement 2, conference abstract 530.*

* cited by examiner

Primary Examiner — Russell S Negin

(57) ABSTRACT

The present invention relates to calibration and normalization systems and methods for ensuring the quality of radiopharmaceuticals during the synthesis thereof, such as radiopharmaceuticals used in Positron Emission Tomography (PET) and Single-Photon Emission Computed Tomography (SPECT).

20 Claims, 15 Drawing Sheets

| Time Stamp | Seconds | Reactor heater setpoint | Reactor heater temperature | N2 pressure setpoint (in mbar) | N2 pressure measure (in mbar) | Vacuum setpoint (in mbar) | Vacuum measure (in mbar) |
|---|---|---|---|---|---|---|---|
| 9/29/2010 8:56:03 A | 1 | 0 | 26 | 500 | 736 | 400 | 226 |
| 9/29/2010 8:56:04 A | 2 | 0 | 26 | 500 | 529 | 400 | 337 |
| 9/29/2010 8:56:05 A | 3 | 0 | 26 | 500 | 513 | 400 | 427 |
| 9/29/2010 8:56:06 A | 4 | 0 | 26 | 500 | 511 | 400 | 412 |
| 9/29/2010 8:56:07 A | 5 | 0 | 26 | 500 | 507 | 400 | 431 |
| 9/29/2010 8:56:08 A | 6 | 0 | 26 | 500 | 504 | 400 | 430 |
| 9/29/2010 8:56:09 A | 7 | 0 | 26 | 500 | 501 | 400 | 429 |
| 9/29/2010 8:56:10 A | 8 | 0 | 26 | 500 | 499 | 400 | 429 |
| 9/29/2010 8:56:11 A | 9 | 0 | 26 | 500 | 507 | 400 | 428 |
| 9/29/2010 8:56:12 A | 10 | 0 | 26 | 500 | 512 | 400 | 428 |
| 9/29/2010 8:56:13 A | 11 | 0 | 26 | 500 | 510 | 400 | 428 |
| 9/29/2010 8:56:14 A | 12 | 0 | 26 | 500 | 508 | 400 | 427 |
| 9/29/2010 8:56:15 A | 13 | 0 | 26 | 500 | 506 | 400 | 427 |
| 9/29/2010 8:56:16 A | 14 | 0 | 26 | 500 | 505 | 400 | 427 |
| 9/29/2010 8:56:17 A | 15 | 0 | 26 | 500 | 504 | 400 | 426 |
| 9/29/2010 8:56:18 A | 16 | 0 | 26 | 500 | 502 | 400 | 426 |
| 9/29/2010 8:56:19 A | 17 | 0 | 26 | 500 | 501 | 400 | 426 |
| 9/29/2010 8:56:20 A | 18 | 0 | 26 | 500 | 499 | 400 | 425 |
| 9/29/2010 8:56:21 A | 19 | 0 | 26 | 500 | 498 | 400 | 425 |
| 9/29/2010 8:56:22 A | 20 | 0 | 26 | 500 | 516 | 400 | 421 |
| 9/29/2010 8:56:23 A | 21 | 0 | 26 | 500 | 510 | 400 | 414 |
| 9/29/2010 8:56:24 A | 22 | 0 | 26 | 500 | 502 | 400 | 408 |
| 9/29/2010 8:56:25 A | 23 | 0 | 26 | 500 | 505 | 400 | 408 |
| 9/29/2010 8:56:26 A | 24 | 0 | 26 | 500 | 504 | 400 | 398 |
| 9/29/2010 8:56:27 A | 24 | 0 | 26 | 500 | 504 | 400 | 429 |
| 9/29/2010 8:56:28 A | 26 | 0 | 26 | 500 | 500 | 400 | 422 |
| 9/29/2010 8:56:29 A | 27 | 0 | 26 | 500 | 512 | 400 | 417 |
| 9/29/2010 8:56:30 A | 28 | 0 | 26 | 500 | 501 | 400 | 413 |
| 9/29/2010 8:56:31 A | 29 | 0 | 26 | 500 | 511 | 400 | 409 |
| 9/29/2010 8:56:32 A | 30 | 0 | 26 | 500 | 500 | 400 | 405 |
| 9/29/2010 8:56:33 A | 31 | 0 | 26 | 500 | 510 | 400 | 400 |
| 9/29/2010 8:56:34 A | 32 | 0 | 26 | 500 | 499 | 400 | 425 |
| 9/29/2010 8:56:35 A | 33 | 0 | 26 | 500 | 508 | 400 | 423 |
| 9/29/2010 8:56:36 A | 34 | 0 | 26 | 500 | 497 | 400 | 418 |
| 9/29/2010 8:56:37 A | 35 | 0 | 26 | 500 | 506 | 400 | 413 |
| 9/29/2010 8:56:38 A | 36 | 0 | 26 | 500 | 496 | 400 | 409 |
| 9/29/2010 8:56:39 A | 37 | 0 | 26 | 500 | 504 | 400 | 405 |

FIG. 2B

| Syringe N°1 set-point | Syringe N°1 measure | Syringe N°2 set-point | Syringe N°2 measure | Syringe N°3 set-point | Syringe N°3 measure | Activity detector N°1 | Activity detector N°2 | Activity detector N°3 | Activity detector N°4 | Activity detector N°5 |
|---|---|---|---|---|---|---|---|---|---|---|
| 0 | 0 | 0 | 0 | 0 | 0 | 3750 | 3988 | -1 | 222 | 214 |
| 0 | 0 | 0 | 0 | 0 | 0 | 3830 | 3941 | -1 | 237 | 222 |
| 0 | 0 | 0 | 0 | 0 | 0 | 3885 | 3949 | -1 | 222 | 222 |
| 0 | 0 | 0 | 0 | 0 | 0 | 5051 | 3877 | -1 | 222 | 229 |
| 0 | 0 | 0 | 0 | 0 | 0 | 8437 | 3750 | -1 | 222 | 229 |
| 0 | 0 | 0 | 0 | 0 | 0 | 11458 | 3663 | -1 | 222 | 222 |
| 0 | 0 | 0 | 0 | 0 | 0 | 15376 | 3584 | -1 | 237 | 222 |
| 0 | 0 | 0 | 0 | 0 | 0 | 18825 | 3497 | -1 | 253 | 214 |
| 0 | 0 | 0 | 0 | 0 | 0 | 22513 | 3401 | -1 | 253 | 206 |
| 0 | 0 | 0 | 0 | 0 | 0 | 26375 | 3306 | -1 | 229 | 206 |
| 0 | 0 | 0 | 0 | 0 | 0 | 30411 | 3156 | -1 | 229 | 206 |
| 0 | 0 | 0 | 0 | 0 | 0 | 34495 | 3045 | -1 | 229 | 206 |
| 0 | 0 | 0 | 0 | 0 | 0 | 38682 | 2942 | -1 | 253 | 198 |
| 0 | 0 | 0 | 0 | 0 | 0 | 42901 | 2799 | -1 | 253 | 182 |
| 0 | 0 | 0 | 0 | 0 | 0 | 47135 | 2688 | -1 | 237 | 174 |
| 0 | 0 | 0 | 0 | 0 | 0 | 51426 | 2561 | -1 | 237 | 174 |
| 0 | 0 | 0 | 0 | 0 | 0 | 55716 | 2434 | -1 | 229 | 182 |
| 0 | 0 | 0 | 0 | 0 | 0 | 60093 | 2299 | -1 | 222 | 190 |
| 0 | 0 | 0 | 0 | 0 | 0 | 64470 | 2212 | -1 | 222 | 190 |
| 0 | 0 | 0 | 0 | 0 | 0 | 67214 | 2188 | -1 | 214 | 198 |
| 0 | 0 | 0 | 0 | 0 | 0 | 67936 | 2188 | -1 | 222 | 214 |
| 0 | 0 | 0 | 0 | 0 | 0 | 68134 | 2180 | -1 | 222 | 206 |
| 0 | 0 | 0 | 0 | 0 | 0 | 68198 | 2188 | -1 | 222 | 206 |
| 0 | 0 | 0 | 0 | 0 | 0 | 68245 | 2188 | -1 | 222 | 206 |
| 0 | 0 | 0 | 0 | 0 | 0 | 68261 | 2188 | -1 | 214 | 206 |
| 0 | 0 | 0 | 0 | 0 | 0 | 68269 | 2188 | -1 | 214 | 214 |
| 0 | 0 | 0 | 0 | 0 | 0 | 68277 | 2188 | -1 | 222 | 198 |
| 0 | 0 | 0 | 0 | 0 | 0 | 68285 | 2180 | -1 | 214 | 206 |
| 0 | 0 | 0 | 0 | 0 | 0 | 68245 | 2188 | -1 | 222 | 206 |
| 0 | 0 | 0 | 0 | 0 | 0 | 68190 | 2188 | -1 | 229 | 222 |
| 0 | 0 | 0 | 0 | 0 | 0 | 68237 | 2188 | -1 | 222 | 214 |
| 0 | 0 | 0 | 0 | 0 | 0 | 68237 | 2188 | -1 | 237 | 206 |
| 0 | 0 | 0 | 0 | 0 | 0 | 68237 | 2180 | -1 | 222 | 198 |
| 0 | 0 | 0 | 0 | 0 | 0 | 68174 | 2188 | -1 | 222 | 206 |
| 0 | 0 | 0 | 0 | 0 | 0 | 68190 | 2196 | -1 | 222 | 198 |
| 0 | 0 | 0 | 0 | 0 | 0 | 68190 | 2188 | -1 | 222 | 198 |
| 0 | 0 | 0 | 0 | 0 | 0 | 68198 | 2180 | -1 | 222 | 206 |

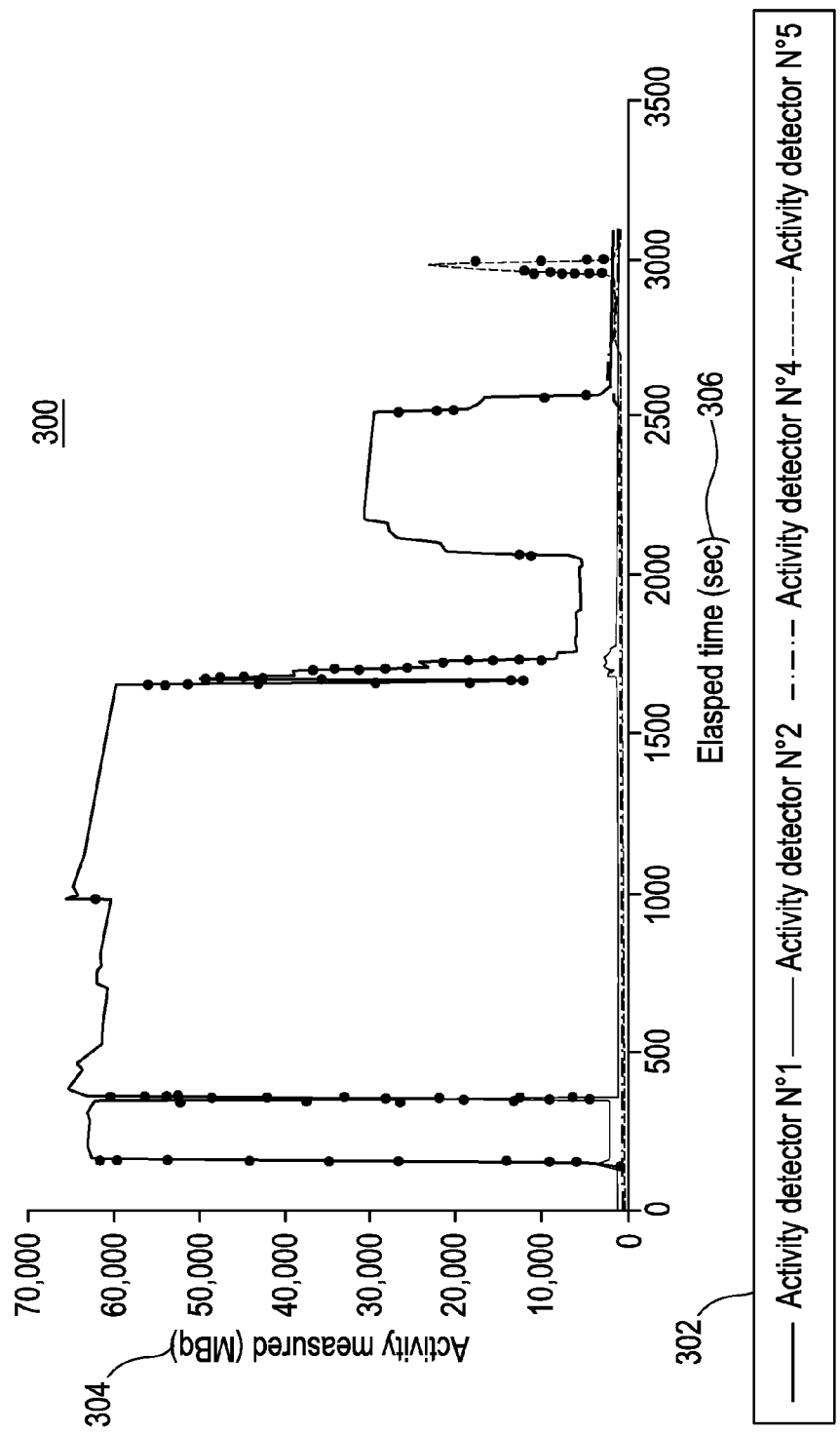

| 602 | SoS (QMA) (MBq) | Difference QMA measured incoming (MBq) | N°2 SoL (MBq) | N°2 EoL (MBq) | N°2 SoC (MBq) | Yield labelling | N°2 EoS (MBq) | Yield conjugation step | Crude yield, activity | Peak signal N°5 (MBq) | SPE recovery (%) | EOP yield, not RCP corrected | Reported yield (%) |
|---|---|---|---|---|---|---|---|---|---|---|---|---|---|
| NMS J177 | 54380 | 13390 | 55627 | 51752 | 28708 | 51.6% | 27882 | 97.1% | 51.3% | 23147 | 83.0% | 42.6% | 40.0 |
| NMS J178 | 57056 | 10474 | 57008 | 53178 | 27707 | 48.6% | 26896 | 97.1% | 47.1% | 23401 | 87.0% | 41.0% | 40.5 |
| NMS J179 | 55222 | 11608 | 56807 | 52631 | 27404 | 48.2% | 26547 | 96.9% | 48.1% | 22433 | 84.5% | 40.6% | 38.6 |
| NMS J180 | 60945 | 10577 | 61073 | 57038 | 29042 | 47.6% | 28731 | 98.9% | 47.1% | 18925 | 65.9% | 31.1% | 31.4 |
| NMS J181 | 57056 | 10484 | 56340 | 52457 | 25280 | 44.9% | 24400 | 96.5% | 42.8% | 20263 | 83.0% | 35.5% | 34.3 |
| NMS J186 | 59937 | 9907 | 59883 | 56166 | 29899 | 49.9% | 28739 | 96.1% | 47.9% | 26104 | 90.8% | 43.6% | 42.6 |
| NMS J187 | 59300 | 10216 | 60497 | 54990 | 29467 | 48.7% | 28466 | 96.6% | 48.0% | 24576 | 86.3% | 41.4% | 40.9 |
| NMS J188 | 62952 | | 64312 | 59488 | 30544 | 47.5% | 29391 | 96.2% | 46.7% | 22948 | 78.1% | 36.5% | 36.0 |

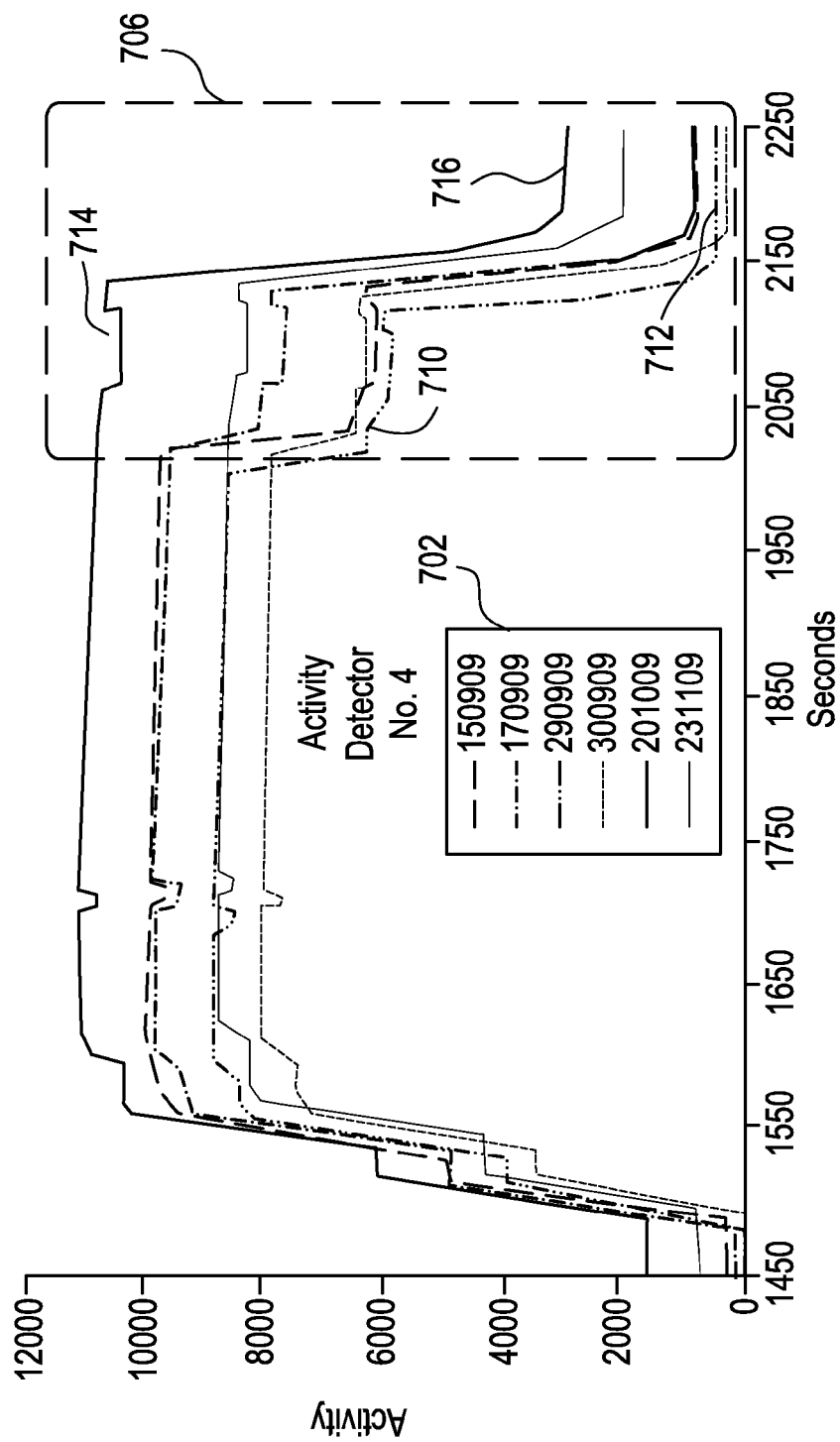

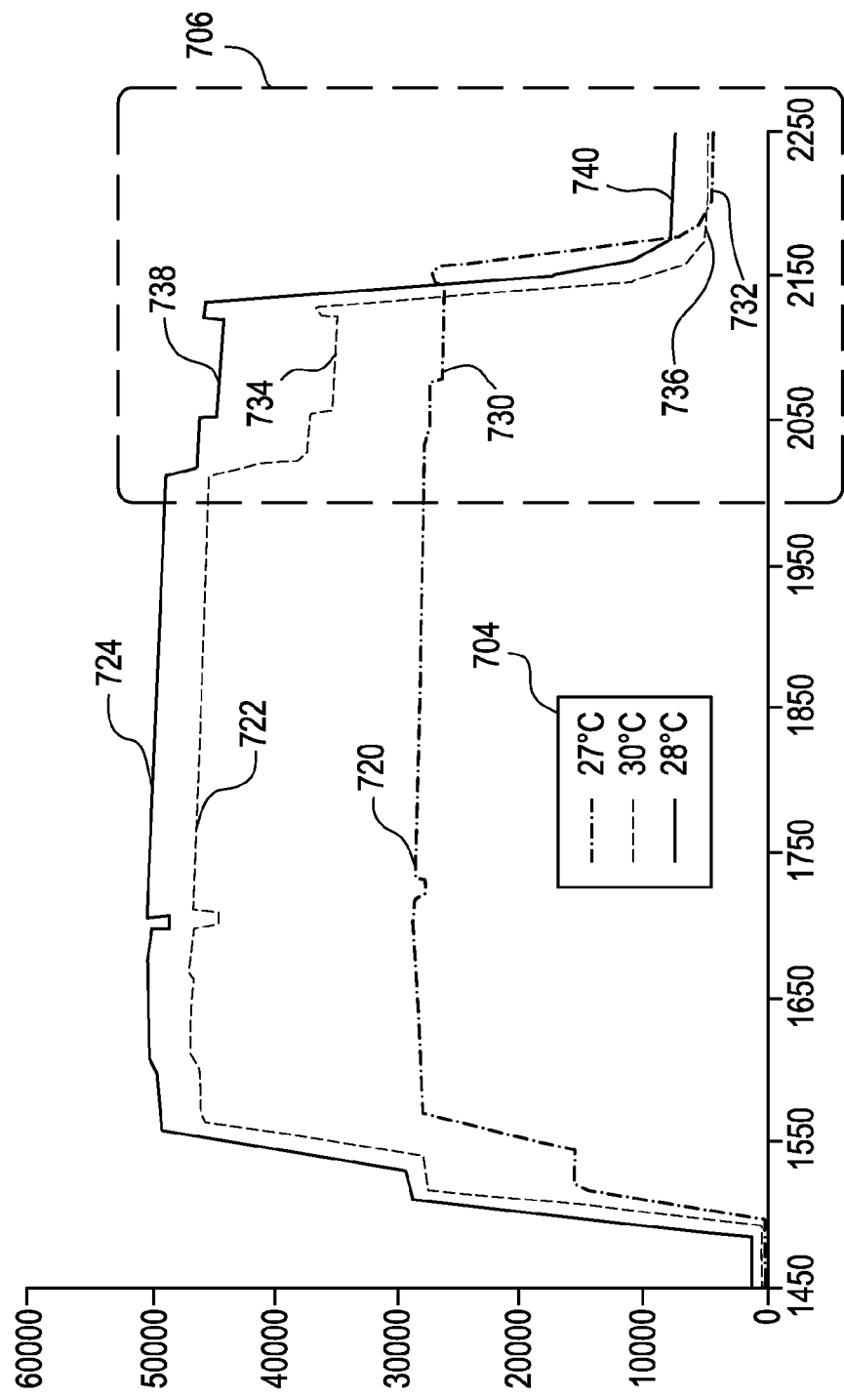

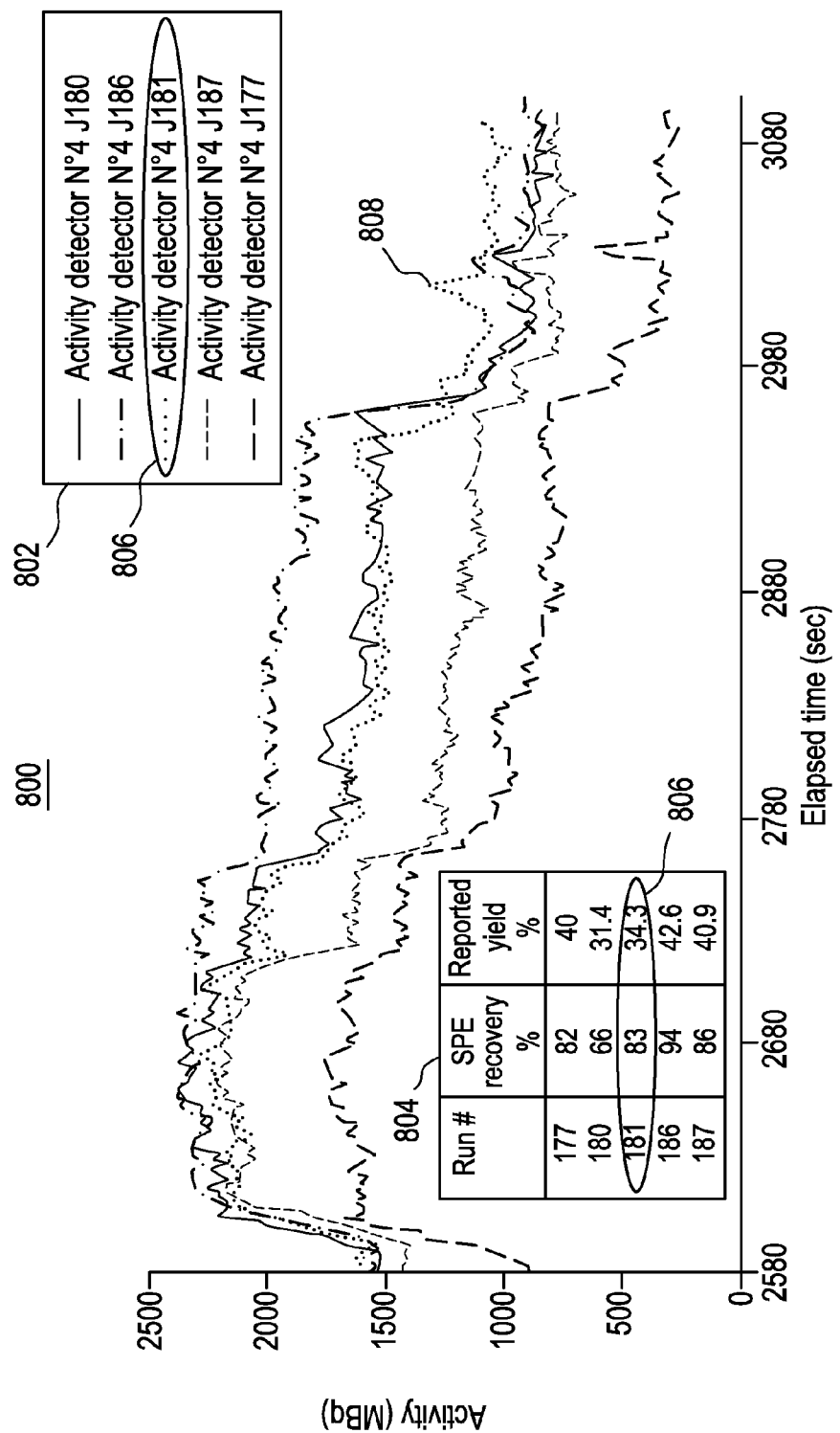

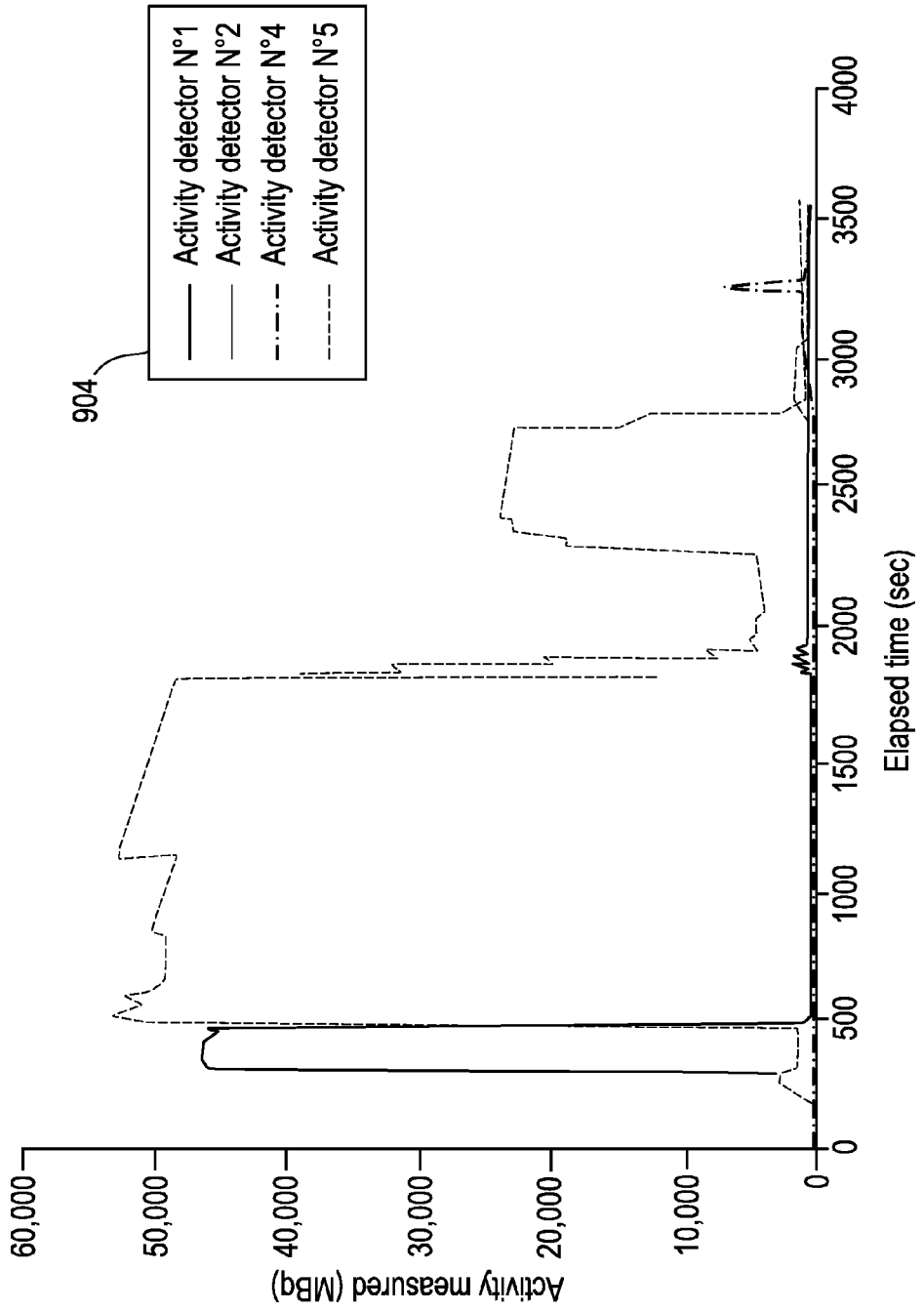

FIG. 10

| | SoS (QMA) (MBq) | Difference QMA measured incoming (MBq) | DATA obtained from log files only | | | | Reported yield (%) | Relative differences between estimated and reported yields % |
|---|---|---|---|---|---|---|---|---|
| | | | N°2 SoL (MBq) | Peak signal N°5 (MBq) | SPE recovery (%) | EOP yield, not RCP corrected | | |
| NMS J177 | 54380 | 13390 | 55627 | 23147 | 83.0% | 42.6% | 40.0 | -6.4 |
| NMS J178 | 57056 | 10474 | 57008 | 23401 | 87.0% | 41.0% | 40.5 | -1.3 |
| NMS J179 | 55222 | 11608 | 56807 | 22433 | 84.5% | 40.6% | 38.6 | -5.3 |
| NMS J180 | 60945 | 10577 | 61073 | 18925 | 65.9% | 31.1% | 31.4 | 1.2 |
| NMS J181 | 57056 | 10484 | 56340 | 20263 | 83.0% | 35.5% | 34.3 | -3.5 |
| NMS J186 | 59937 | 9907 | 59883 | 26104 | 90.8% | 43.6% | 42.6 | -2.2 |
| NMS J187 | 59300 | 10216 | 60497 | 24576 | 86.3% | 41.4% | 40.9 | -1.3 |
| NMS J188 | 62952 | | 64312 | 22948 | 78.1% | 36.5% | 36.0 | -1.3 |
| UI 11014 | 70694 | | 78500 | 9411 | 27.2% | 13.3% | 17.9 | 25.6 |
| UI 11015 | 70228 | | 81750 | 12859 | 35.7% | 18.3% | 25.6 | 28.5 |
| UI 11016 | 46265 | | 52346 | 6793 | 29.5% | 14.7% | 22.3 | 34.2 |
| TGC 00316 | 62588 | | 74457 | 22238 | 62.2% | 35.5% | 38.7 | 8.2 |

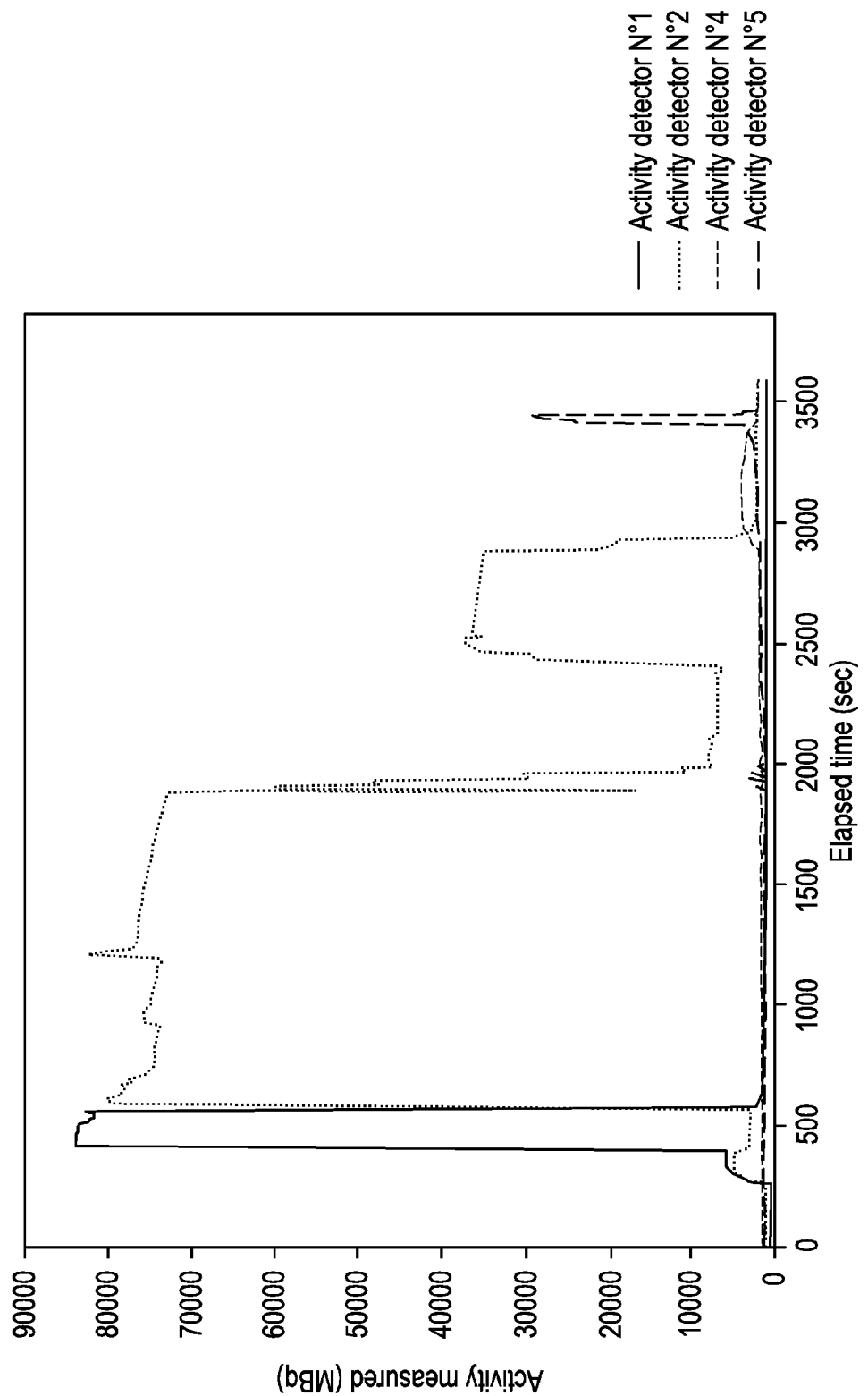

CALIBRATION AND NORMALIZATION SYSTEMS AND METHODS FOR RADIOPHARMACEUTICAL SYNTHESIZERS

This application is a filing under 35 U.S.C. 371 of international application number PCT/US2012/057930, filed Sep. 28, 2012, published on Apr. 4, 2013 as WO 2013/049577, which claims priority to U.S. provisional patent application No. 61/541,246 filed Sept. 30, 2011.

FIELD OF THE INVENTION

The present invention relates to calibration and normalization systems and methods for ensuring the quality of radiopharmaceuticals during the synthesis thereof, such as radiopharmaceuticals used in Positron Emission Tomography (PET) and Single-Photon Emission Computed Tomography (SPECT).

BACKGROUND OF THE INVENTION

PET and SPECT imaging systems are increasingly used for detection of diseases and are useful in providing early detection and a definite diagnosis for such diseases (e.g., disease states within oncology and neurology). For example, currently, a large percentage of PET and SPECT tests are related to cancer detection and early Alzheimer detection. These diseases require early diagnosis to allow a timely and effective treatment.

PET and SPECT imaging systems create images based on the distribution of positron-emitting isotopes and gamma emitting isotopes, respectively, in the tissue of a patient. The isotopes are typically administered to a patient by injection of radiopharmaceuticals including a probe molecule having a positron-emitting isotope, e.g., carbon-11, nitrogen-13, oxygen-15, or fluorine-18, or a gamma radiation emitting isotope, e.g. technetium-99m. The radiopharmaceutical is readily metabolized, localized in the body or chemically binds to receptor sites within the body. Once the radiopharmaceutical localizes at the desired site (e.g., chemically binds to receptor sites), a PET or SPECT image is generated.

Examples of known radiopharmaceuticals include $^{18}$F-FLT ($[^{18}$F]fluorothymidine), $^{18}$F-FDDNP (2-(1-{6-[(2-[$^{18}$F]fluoroethyl)(methyl)amino]2-naphthyl}ethylidene)malonitrile), $^{18}$F-FHBG (9-[4-[$^{18}$F]fluoro-3-(hydroxymethyl) butyl]guanine or [$^{18}$F]-penciclovir), $^{18}$F-FESP ([$^{18}$F]-fluoroethylspiperone), $^{18}$F-p-MPPF (4-(2-methoxyphenyl)-1-[2-(N-2-pyridinyl)-p-[18p]fluorobenzamido]ethylpiperazine) and $^{18}$F-FDG ([$^{18}$F]-2-deoxy-2-fluoro-D-glucose).

Radioactive isotopes in radiopharmaceuticals are isotopes exhibiting radioactive decay, for example, emitting positrons. Such isotopes are typically referred to as radioisotopes or radionuclides. Exemplary radioisotopes include $^{18}$F, $^{124}$I, $^{11}$C, $^{13}$N and $^{15}$O, which have half-lives of 110 minutes, 4.2 days, 20 minutes, 10 minutes, and 2 minutes, respectively.

Because radioisotopes have such short half-lives, the synthesis and purification of the corresponding radiopharmaceutical must be rapid and efficient. Any quality control (QC) assessments on the radiopharmaceutical must also take place in a short period of time. Preferably, these processes (i.e., synthesis, purification, and QC assessment) should be completed in a time well under the half-life of the radioisotope in the radiopharmaceutical. Presently, QC assessments (e.g., chemical yield and chemical purity) may be relatively slow mainly due to the fact that they are conducted manually. Accordingly, there is a need for systems, components, and methods for capturing, analyzing, and interpreting data obtained during the synthesis and purification processes of a radiopharmaceutical to ensure that those synthesis and purification are proceeding efficiently to produce quality radiopharmaceuticals in a desired quantity. From this analysis, changes can be implemented before, during or after the synthesis and/or purification of the radiopharmaceutical to correct any deficiencies, as they occur during the radiopharmaceutical's synthesis. The embodiments of the present invention provide such systems, components, and methods, which allow for capture and analysis of real data, as well as the correction of deficiencies, during the synthesis of the radiopharmaceutical. A site to site comparison can also be performed to enable comparison across geographically diverse sites conducting radiopharmaceutical synthesis.

SUMMARY OF THE INVENTION

An exemplary embodiment includes a method of monitoring a radiopharmaceutical synthesis process. Data relating to the radiopharmaceutical synthesis process is received from a radiopharmaceutical synthesizer. The data is analyzed. One or more characteristics of the data is identified wherein the one or more characteristics pertain to quality control factors relating to the radiopharmaceutical synthesis process. The one or more characteristics of the data are extracted. The extracted data is analyzed.

Another exemplary embodiment includes a method for performing radiosynthesis with an automated radiosynthesizer having a number of individual activity detectors operably associated therewith. The method includes providing a calibration standard having a source of gamma radiation, desirably a positron-emitting isotope, where the gamma source is of both a known activity and a known time decay correlation factor, in the vicinity of each activity detector of the radiosynthesizer at defined time intervals. The activity data from each activity detector is recorded as the calibration standard is in the vicinity thereof. The correlation factor $C_f$ for each individual activity detector is determined as:

$$C_f = (x/y)*z$$

where x is the known activity of the calibration standard, y is the activity data recorded at the particular individual activity detector, and z is a defined decay by time decay correlation factor for the calibration standard. The method synthesizes a tracer with the radiosynthesizer where the synthesis includes the step of applying the correlation factor $C_f$ determined for each individual activity detector to the activity readings by that individual activity detector which are detected as the tracer is synthesized.

Yet another exemplary embodiment of the present invention includes a method of calibrating an automated radiosynthesizer having a number of individual activity detectors operably associated therewith. The method includes providing a calibration standard having a source of gamma radiation, desirably a positron-emitting isotope, where the gamma source is of both a known activity and a known time decay correlation factor, in the vicinity of each activity detector of the radiosynthesizer at defined time intervals. The activity data from each activity detector is recorded as the calibration standard is in the vicinity thereof. The correlation factor $C_f$ for each individual activity detector is determined as:

$$C_f = (x/y)*z$$

where x is the known activity of the calibration standard, y is the activity data recorded at the particular individual activity detector, and z is a defined decay by time decay correlation factor for the calibration standard.

BRIEF DESCRIPTION OF THE DRAWINGS

FIG. 2A depicts an exemplary first portion of a data collection file according to an exemplary embodiment of the invention.

FIG. 2B depicts an exemplary second portion of a data collection file according to an exemplary embodiment of the invention.

FIG. 3 depicts a plot of data collection file data according to an exemplary embodiment.

FIG. 6 depicts a set of yield predictions and reported yields according to an exemplary embodiment.

FIGS. 7A and 7B depict a section of a plot of data collection file data according to an exemplary embodiment.

FIG. 8 depicts a section of a plot of a series of traces of data collection file data during the final purification step according to an exemplary embodiment.

FIGS. 9A, 9B, and 9C depict traces of data collection file data from different synthesis sites according to an exemplary embodiment.

FIG. 10 depicts a data table corresponding to the traces of FIGS. 9A-C according to an exemplary embodiment.

FIG. 11 depicts an activity plot or trace for an automated synthesizer after calibration of the synthesizer's detectors according to an exemplary embodiment of the present invention.

Figure 1:
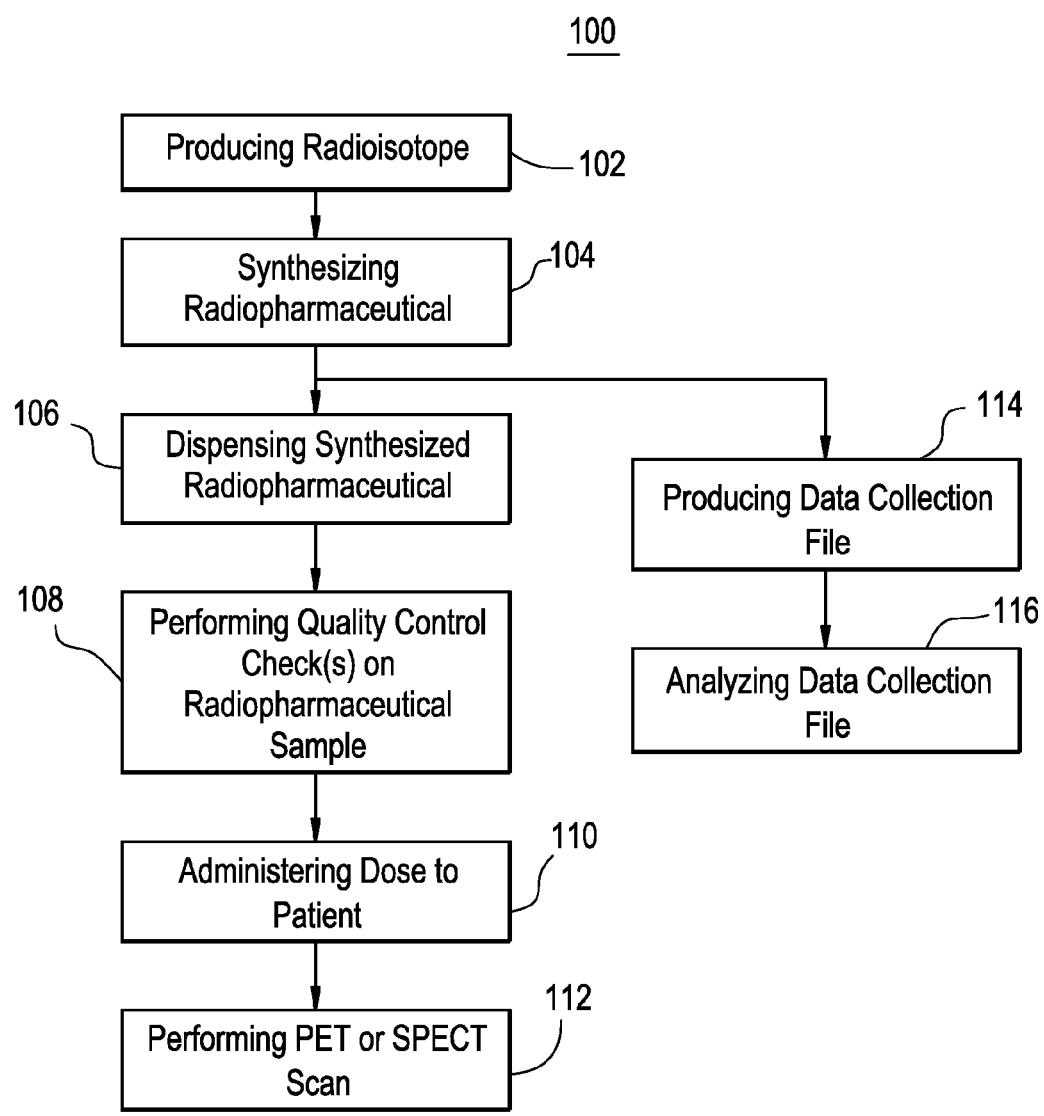
FIG. 1 depicts a method for producing and using a PET or SPECT imaging agent and extracting data collection file data according to an exemplary embodiment of the invention.

These and other embodiments and advantages of the invention will become apparent from the following detailed description, taken in conjunction with the accompanying drawings, illustrating by way of example the principles of the various exemplary embodiments of the invention.

DETAILED DESCRIPTION OF THE PREFERRED EMBODIMENTS

It will be readily understood by those persons skilled in the art that the embodiments of the inventions described herein are capable of broad utility and application. Accordingly, while the invention is described herein in detail in relation to the exemplary embodiments, it is to be understood that this disclosure is illustrative and exemplary of embodiments and is made to provide an enabling disclosure of the exemplary embodiments. The disclosure is not intended to be construed to limit the embodiments of the invention or otherwise to exclude any other such embodiments, adaptations, variations, modifications and equivalent arrangements.

The following descriptions are provided of different configurations and features according to exemplary embodiments of the invention. These configurations and features may relate to providing systems and methods for quality control of radiopharmaceuticals and other compounds or formulations containing radioisotopes. While certain nomenclature and types of applications or hardware are described, other names and application or hardware usage is possible and the nomenclature provided is done so by way of non-limiting examples only. Further, while particular embodiments are described, these particular embodiments are meant to be exemplary and non-limiting and it further should be appreciated that the features and functions of each embodiment may be combined in any combination as is within the capability of one of ordinary skill in the art.

The figures depict various functionality and features associated with exemplary embodiments. While a single illustrative block, sub-system, device, or component is shown, these illustrative blocks, sub-systems, devices, or components may be multiplied for various applications or different application environments. In addition, the blocks, sub-systems, devices, or components may be further combined into a consolidated unit. Further, while a particular structure or type of block, sub-system, device, or component is shown, this structure is meant to be exemplary and non-limiting, as other structure may be able to be substituted to perform the functions described.

Exemplary embodiments of the invention relate to automated synthesis systems for radiopharmaceuticals, such systems also referred to and used herein as 'synthesizers' or 'radiosynthesizers'. The term 'automated' denotes that the synthesizer is programmed to cause performance of certain steps in the radiosynthesis operation for producing a tracer. The synthesis system may produce radiopharmaceuticals for use with either PET or SPECT scanners. For example, the synthesis system may be the FASTlab® system from GE Healthcare, Liege, Belgium. The use of the FASTlab system in examples described herein is meant to be exemplary and non-limiting. It should be appreciated that the embodiments described herein may be used with a variety of synthesis systems manufactured by companies other than GE Healthcare. It should further be appreciated that the use of the term "radiopharmaceutical", "radiotracer", "PET tracer", or "SPECT tracer" herein is meant to be exemplary and non-limiting and the mention of one term does not exclude substitution of the other terms in the described embodiment. Additionally, the term "activity detector" refers to a detection instrument incorporated into an automated synthesizer which detects radioactivity from the gamma source, e.g., the positron-emitting isotope, in the vicinity thereof. Such activity detectors are well known in the art.

The present invention improves the automated synthesis of radiopharmaceuticals by normalizing the activity detectors on the automated synthesis device used. This normalizing may be performed prior to synthesis of a radiopharmaceutical by passing, for example, an unacted-upon radioactive isotope, desirably the same isotope as used in the radiotracer, by each detector and then accounting for losses during the transfer of the isotope during a synthesis run. Since performance variations have been observed for an automated synthesis device, such as a FASTlab synthesizer, at different local manufacturing/synthesis sites, the present invention provides a method for ensuring that synthesis at each synthesis device is optimized for its production runs. The present invention thus provides both a method for performing radiosynthesis with an automated radiosynthesizer, but also a method of calibrating an automated radiosynthesizer, in each case where the radiosynthesizer includes one or more activity detectors thereon.

In a method of the present invention for performing radiosynthesis with an automated radiosynthesizer having one or more individual activity detectors operably associated therewith, the method includes providing a calibration standard having a source of gamma radiation, such as a positron-emitting isotope, where the isotope is of both a known activity and a known time decay correlation factor, in the vicinity of each activity detector of the radiosynthesizer at defined time intervals. The activity data from each activity detector is recorded as the calibration standard is in the vicinity thereof. The correlation factor $C_f$ for each individual activity detector is determined as $$C_f = (x/y)*z$$

where x is the known activity of the calibration standard, y is the activity data recorded at the particular individual activity detector, and z is a defined decay by time decay correlation factor for the calibration standard. The method synthesizes a tracer with the radiosynthesizer where the synthesis includes the step of applying the correlation factor $C_f$ determined for each individual activity detector to the activity readings by that individual activity detector which are detected as the tracer is synthesized.

In a method of the present invention for calibrating an automated radiosynthesizer having a number of individual activity detectors operably associated therewith, the method includes providing a calibration standard having a positron-emitting isotope, where the isotope is of both a known activity and a known time decay correlation factor, in the vicinity of each activity detector of the radiosynthesizer at defined time intervals. The activity data from each activity detector is recorded as the calibration standard is in the vicinity thereof. The correlation factor $C_f$ for each individual activity detector is determined as:

$$C_f = (x/y)*z$$

where x is the known activity of the calibration standard, y is the activity data recorded at the particular individual activity detector, and z is a defined decay by time decay correlation factor for the calibration standard.

The present invention intends the phrase "in the vicinity of" to denote that the calibration standard is brought within the detection range of an activity detector. Desirably, the calibration standard is brought as close to each activity detector as possible. More desirably, the calibration standard is brought as close to each activity detector as the activity will be brought during a synthesis run. For example, the present invention contemplates that calibration could be performed using either a normal synthesis cassette or a specially designed cassette which solely provides for calibrating the activity detectors on the automated synthesizer. As the location of the activity detector on the synthesizer is fixed, it is desirable to provide the standard at a location relative to the detector which emulates where a synthesis cassette would provide it during a synthesis operation, thereby limiting the geometric effects of imprecisely locating the standard relative to the detector. By way of illustration and not of limitation, where the activity detector is collimated, the present invention desirably tailors the location of the calibration standard to be in the same vicinity of the activity detector as the synthesis cassette will provide the gamma source during tracer synthesis operations on the synthesizer so as to minimize the deviation in the amount of activity detected from the actual value.

For either method of the present invention, the calibration standard desirably includes the same radioisotope as is used in the radiopharmaceutical being or to be synthesized, including, by way of illustration and not of limitation, a radioisotope selected from the group of $^{18}$F, $^{11}$C, $^{99m}$Tc, $^{67}$Ga, $^{99}$Mo, and $^{123}$I. The radiopharmaceutical synthesizer is configured to produce a particular radiopharmaceutical for use in conjunction with conducting a SPECT or a PET scan. Desirably, the method further includes the step of building a data collection file having a set of data recorded at a known time interval, e.g., one second intervals, at each activity detector during a radiopharmaceutical synthesis. The present invention provides for the calibration of all of the detectors with respect to each other on a single automated synthesizer. The present invention thus provides for more precise yield calculation at the dispensing of the product as well as at key points during the synthesis process.

In either method of the present invention, the calculation of the correlation factors $C_f$ for each activity detector may be performed manually and applied to the activity detector readings, although the calculation is desirably performed automatically. Similarly, the application of the correlation factor for each activity detector may be performed manually, either by calculating a corrected activity reading and/or a corrected yield calculation, or by entering the correlation factor either manually or automatically into a computer controlling the synthesizer. Additionally, application of the correlation factor may be performed automatically by a computer on board the synthesizer. That is, the present invention further contemplates providing a non-transitory computer-readable storage medium with an executable program for performing the step of calculating the correlation factor for an activity detector according to either method of the present invention, such that execution of the computer-readable program code causes a processor to perform the step of determining the correlation factor for an activity detector on a radiosynthesizer for either method of the present invention. Alternatively, the present invention provides a computer-readable storage medium that includes computer-readable program code including instructions for applying a correlation factor to the output of an activity detector of a radiosynthesizer, such that execution of the computer-readable program code causes a processor to perform the applying step of the synthesis method of the present invention.

The present invention contemplates that the provision of the calibration standard may be performed by connecting a cassette to the radiosynthesizer. Such a cassette desirably emulates the cassette employed by the synthesizer. By way of illustration and not of limitation, where the radiosynthesizer is a FASTlab synthesizer, the design emulates that of a FASTlab cassette so as to include valves and conduits for conducting the calibration standard therethrough to each activity detector. Such a cassette is desirably operable by the radiosynthesizer in a manner similar to an actual synthesis cassette. That is, the cassette includes a manifold, conduits, stopcock valves which engage the FASTlab synthesizer, as well as syringe pumps and motive fluid ports which, when operated on by the synthesizer, direct the calibration standard to each activity detector. Thus, the calibration standard may be directed into the cassette in the same manner as the radioisotope used in a radiopharmaceutical. The calibration standard may be delivered from a cyclotron where its activity and activity decay profile may be determined. For example, the calibration standard may be directed into the input port of the cassette and directed to a QMA cartridge in the vicinity of a first activity detector of the synthesizer. The calibration standard may also be, after passing past or in the vicinity of each of the activity detectors at the desired time, directed out of the cassette through an output port of the cassette. The cassette and the method of the present invention are thus able to direct the calibration standard to each of the activity detectors of the synthesis device as that synthesis device would during a normal synthesis operation.

The present invention is scalable to the actual synthesis devices used, and will be able to direct the calibration standard next to, or in the vicinity of, each activity detector of the synthesis device, whether it includes one or more activity detectors. That is, the present invention is scalable to employ with a radiosynthesizer having, by way of illustration and not of limitation, four, five, or six or more activity detectors.

During the automated synthesis of radiopharmaceutical, a data collection file for the synthesis run is generally produced. For example, for every radiopharmaceutical synthesis run on a FASTlab system, a unique log file for the run is produced. This file consists of data collected at various points in the synthesis using various sensors and activity detectors that are a part of the process, such as radioactivity detectors. The data in the data collection file may be collected at certain time intervals. For example, in a FASTlab system, a log file consists of data collected at one second intervals throughout the entire synthesis with the data being measured by up to six different radioactivity detectors, as well as set values and measured values for the programmable process parameters in the FASTlab sequence file (e.g., reactor temperature, pressure, and syringe positions). It should be understood that the data collection intervals may be adjusted and may be measured at different intervals other than every second (e.g., every five seconds or every ten seconds). Data may be collected from different sensors or radioactivity detectors at different intervals for each (e.g., every second at one detector and every five seconds at another).

The data in the data collection file, such as a log file, when presented graphically, represents a diagnostic "fingerprint" for any given FASTlab synthesis run. The fingerprint of a successful synthesis run can be established based on established data. Subsequent synthesis runs may be then compared to the fingerprint of the successful synthesis run in order to compare the performance of the synthesis system. Deficiencies or problem areas in the synthesis process can then be identified and appropriate action taken. For example, deviations from the "good" or "acceptable" fingerprint can be determined and potential problem areas in the synthesis process can be identified, such as a which step of the process is experiencing a problem or not performing up to expected standards. Using this technique, synthesizer processes across multiple sites may also be compared. As part of such comparison, it may be necessary to calculate a correlation or normalization factor, as described below, to enable the data from each run to be moved to a common baseline to ensure an accurate comparison between different synthesizers at different locations.

Accordingly, the data collection file can provide valuable information about each synthesis run and may be used, for example, to monitor variations between identical runs; to see the effect of modifications to the synthesis runs; for trouble shooting; and as a tool during PET tracer manufacturing set-up. Useful information may therefore be obtained through analysis and correlation of the data collection file data. For example, quality control information, such as, for example, yield and purity, may be extracted from the data collection file data and analyzed. Through such analysis, the radiopharmaceutical synthesis process may be adjusted based on this quality control information. This analysis process may simplify quality control procedures through the potential elimination of post-production quality control tests since the results can be determined from the synthesis process itself.

In addition to the information from sensors and activity detectors, such as the radioactivity detectors, the data collection file may contain set values and real, or measured, values for the programmable process parameters in the synthesizer's sequence file. For example, a FASTlab log file contains measurements of data from the following programmable process parameters: reactor heater temperature, nitrogen pressure, vacuum, and syringe position. Accordingly, the use of information from the activity detectors in combination with process parameters in the data collection file adds valuable information regarding given steps and actions in the process.

According to other exemplary embodiments, using activity detector readings obtained from data collection files, the synthesizer reaction performance may be monitored. However, as described hereinabove, radioactivity detector measurements need to be corrected and correlated in order to account for variation in readings amongst different synthesizers located at different locations or sites. In order to perform such a correction, a calibration or normalization process is used to standardize the process data to enable comparison on an equivalent baseline. According to an exemplary embodiment, a basic sequence for the synthesizer is used where a sample with a known amount of radioactivity is passed through the synthesizer in the vicinity of the different radioactivity detectors. A correlation factor for each detector is then calculated based on the results compared to the known radioactivity amount and used during the data analysis to monitor the synthesizer process performance. Once instruments at different locations are calibrated or normalized, the resulting data can be collected and further normalized to account for variations at the different locations. In doing so, data collected from the different locations can be meaningfully compared. This collected data can be centrally analyzed and stored in order to provide various support functions to the different locations such as troubleshooting and customer service.

During the above process, the sample is passed throughout the synthesizer fluid path and the activity is read at each radioactivity detector. During the process, when comparing two sites, say, sites A and B, each having a synthesizer, the data collection file may show that all detectors in A read as expected, but one detector, for example, detector 5 at B reads 10% below what is expected. If it is known that the detector is functioning properly and is aligned properly, then the presumption is that there is a systematic error associated with that detector that causes it to read low. The data is collected from sites A and B at a central data collection site. The central collection site would use the data to normalize the data from the detectors at site B upwards by 10% so that the data for the same detector at site A can be compared to the data from site B. Once calibrated, sites A and B proceed with synthesis.

Each synthesizer typically generates a data collection file during production of a radiopharmaceutical. The contents of the data collection file are transmitted to the same central data collection site either in real time or at some point after the synthesis run is complete. Provided the same radiopharmaceutical is being synthesized at each site, the data generated from sites A and B could be compared. The data for site B, of course, would have to be normalized up to account for the fact that its detector 5, is known to read low. The data may show production trends or issues with each site. For example, the data collection file data could show that there was a good solid phase extraction (SPE) recovery, but a low reported yield in the synthesizer at site A. These data may then form the basis for troubleshooting the synthesizer at site A. Upon analysis of the data, a conclusion may be drawn with regard to the problem at site A. For example, the conclusion could be that there was a low yield for the radiolabelling step or some other synthesizer step.

The data collection file data may serve a number of uses. Exemplary, non-limiting uses may include:

Process development, including tuning of purification processes in a synthesizer, including the SPE process(es);

Robustness testing: a robust process would show little deviation from run to run since the graphical representation of the data for each of the radioactivity detectors are like "fingerprints" of the process;

Troubleshooting: problems can be spotted and pinpointed in the radiosynthesis from the trends of the radioactivity detectors deviating from a successful production based on established data;

Support PET tracer manufacturing site set-up;

Ensuring production quantity matches the patient need (e.g., ensuring that the proper number of patient doses is produced);

Identification of trends of the radioactivity detectors at various sites to determine performance of different synthesizers;

Identification of synthesizer hardware problems;

Identification of synthesizer sequence file programming issue(s);

Simplified post-synthesis quality control;

Providing remote customer support; and

Normalization of data collection files, e.g., log files.

FIG. 1 depicts a flow chart of a method of synthesizing and using a PET or SPECT imaging agent and extracting data collection file data according to an exemplary embodiment of the invention. The method 100 as shown in FIG. 1, may be executed or otherwise performed by one or a combination of various systems, components, and subsystems, including a computer implemented system. Each block shown in FIG. 1 represents one or more processes, methods, and/or subroutines carried out in the exemplary method 100.

At block 102, a radioisotope is produced. The radioisotope (e.g., $^{18}$F or $^{11}$C) is typically produced using a cyclotron (e.g., GE PETtrace 700 cyclotron) for PET radioisotopes or using a generator for SPECT radioisotopes (e.g., to produce the $^{99m}$Tc). The cyclotron or generator may be located at a manufacturing site or it may be located in proximity to the scanner. Locating the cyclotron or generator on-site with the PET or SPECT scanner minimizes transportation time for the radioisotope. It should be appreciated that while "PET" and "SPECT" are referred to herein such examples are exemplary and the mention of one does not preclude application to the other.

At block 104, a radiopharmaceutical is synthesized using the radioisotope. A synthesizer is used to combine the radioisotope with a radioligand. The result is a radiopharmaceutical. The synthesizer may be manually operated, semi-automated in operation, or fully automated. For example, the GE Healthcare FASTlab system is a fully automated synthesizer. The synthesizer is generally operated in a "hot cell" to shield the operator from the radioactivity of the radioisotope. During the synthesis of the radiopharmaceutical, data can be collected during the process. The data corresponds to radiodetector or sensor measurements at various points in the synthesis process. The data are collected at various time intervals and may be electronically stored. The data may be output or saved in the form a data collection file. The synthesizer may employ a cassette which is mated thereto and contains the various reagents and other equipment, such as syringe pumps and vials, required for the synthesis of the radiopharmaceutical. The cassette may be removable and disposable. Cassettes may be configured to support the synthesis of one or more radiopharmaceuticals.

At block 106, the synthesized radiopharmaceutical is dispensed. The doses of the radiopharmaceutical are dispensed into collecting vials for patient administration and for QC. A sample of the bulk synthesized radiopharmaceutical may be dispensed directly into a QC system and/or cassette for QC testing. Systems and methods of QC testing are shown in PCT Appl. No. US11/2011/048564 filed on Aug. 22, 2011, the contents of which are incorporated herein by reference in their entirety.

At block 108, quality control checks on a radiopharmaceutical sample are performed. There may be one or more QC checks performed. These QC checks may be automated. The QC system may include a cassette having a plurality of components for performing the tests. The cassette may be configured for insertion into a QC system to carry out the QC checks. The QC system may be a stand-alone system or it may be integrated with the synthesizer described above. Radiopharmaceutical doses are dispensed from the synthesizer. Sample(s) from one or more dispensed vials may be selected for QC checks. These samples may be input to the QC system. Alternatively, the QC system may be connected or coupled to the synthesizer such that an appropriate sample may be directly output from the synthesizer to the QC system.

At block 110, a dose from the same production batch as the sample on which the QC tests were conducted is administered to a patient.

At block 112, a PET or SPECT scan is performed on the patient who received the dose.

At block 114, a data collection file is produced from the synthesizer. This file, which contains data collected during the radiopharmaceutical synthesis, is produced. The data collection file may be formatted and contain data as described herein. Alternatively, other formats for the file may be used. For example, the file may be a log file such as produced by the GE Healthcare FASTlab system as described above. The use of the term "data collection file" or "log file" herein is meant to be exemplary and non-limiting, as there are other terms that may be used for such a data collection file with data collected during a radiopharmaceutical process. It should be appreciated that the data collection file may be produced at any point during the synthesis process.

The data collection file may be produced in hard copy format and/or may be stored electronically. For example, the data collection file may be printed by an output device communicatively coupled to the synthesizer, such as a printer. Alternatively, the data collection file may be output or stored in an electronic format. For example, the synthesizer may have an electronic display or be coupled to a computer system for displaying the data collection file in an electronic format. The data collection file may be electronically saved using electronic storage, either internal to the synthesizer or external thereto. For example, the synthesizer may have solid state storage, both temporary, such as random access memory and/or more permanent such as flash memory or hard disk type storage.

It should also be appreciated that the synthesizer may have input devices to allow for user interaction with the system. These input devices may be communicatively coupled to the system. For example, the synthesizer may have a QWERTY type keyboard, an alpha-numeric pad, and/or a pointing input device. Combinations of input devices are possible. The synthesizer may be communicatively coupled to a computer network. For example, the synthesizer may be communicatively coupled to a local area network or similar network. Through such a network connection, the synthesizer may be communicatively coupled to one or more external computers, computer systems, and/or servers. In some embodiments, the synthesizer may be communicatively coupled to the Internet. The synthesizer may be wirelessly connected to the computer network or may be connected by a wired interface. The synthesizer may transmit and receive data over the computer network. For example, the data collection file may be transmitted over the computer network to another computer system or server. This other computer system or server may be remotely located at a geographically separate location from the synthesizer.

Furthermore, the synthesizer may be computer implemented such that synthesizer includes one or more computer processors, power sources, computer memory, and software. As stated above, the synthesizer may be communicatively coupled to one or more external computing systems. For example, the synthesizer may be communicatively coupled through a computer network, either wired or wireless or a combination of both, to an external computer system. The external computer system may provide commands to cause the synthesizer to operate as well as collect and analyze data from the data collection file. This combination of computer hardware and software may enable to the synthesizer to automatically operate and to perform certain collection of data, analysis of the data, and implementation of corrections or factors derived from the data.

At block 116, the data collection is analyzed. In accordance with exemplary embodiments, the data collection file is analyzed as described herein. As part of the analysis, certain factors and information may be gleaned from the data collection file. Using these factors and information, the radiopharmaceutical process may be altered, modified, and/or tuned. For example, the data analysis may determine that the process is not operating efficiently because a low yield is indicated. By way of non-limiting example, this may be indicative of a problem in the reaction vessel. A fix or modification may be implemented. Such a fix or modification may be manually applied by an operator or may be implemented automatically by the synthesizer based on command issued through a computer system. In some embodiments, the system may be completely automatic and no outside intervention is needed to perform an analysis and implement a correction or modification to the process.

FIGS. 2A and 2B depict a data collection file according to an exemplary embodiment. For example, FIGS. 2A and 2B may depict a log file from a FASTlab system. FIG. 2A depicts a first portion 200A of the data collection file and FIG. 2B depicts a second portion 200B of the data collection file. The first and second portions are parts of the data collection file; that is, FIGS. 2A and 2B may be put together side by side to form an exemplary data collection file. Alternatively, the data collection file may be apportioned as depicted, such as being split into multiple sections. It should be appreciated that the data collection file may be divided into different sections than shown. This data collection file may represent the data collection file containing data produced as shown in the method 100, for example.

The data collection file has a header row 202 with labels on each of the data columns therebelow, as shown in FIGS. 2A and 2B. Exemplary column labels in the header row 202 are depicted in FIGS. 2A and 2B. It should be appreciated that additional or less column labels may be contained in the data collection file. Furthermore, the data and the formatting of the data depicted in each of the columns is meant to be exemplary and non-limiting. These data are meant to depict data collected during an exemplary radiopharmaceutical synthesis process for FACBC, which is used as a non-limiting example. As shown in FIG. 2A, the data points are shown at one second intervals. Each of the data columns (labeled by header row 202) represents a point or state in the radiopharmaceutical process. Data collected from different radioactivity detectors is shown (labeled as "Activity Detector No. N," where "N" is the detector number). These radioactivity detectors measure radioactivity in their vicinity. It should be appreciated that the Activity Detectors described herein are positioned in exemplary positions. More or less Activity Detectors may be used and the positioning of the Activity Detectors may be customizable with respect to the synthesizer and the cassette.

FIG. 3 depicts a plot of data collection file data according to an exemplary embodiment. The plot 300 represents a plot of data collection file data, such as the data depicted in the exemplary data collection file of FIGS. 2A and 2B. The plot 300 has a legend 302. As can be seen, the plot 300 is a plot of the Activity Detector data for Activity Detectors Nos. 1, 2, 4, and 5. The plot 300 may plot Activity Measured 304 versus Elapsed Time 306. A detailed explanation of a data collection file plot is provided in FIG. 4 below. The details are equally application to other data collection file plots, such as the plot 300.

Figure 4:
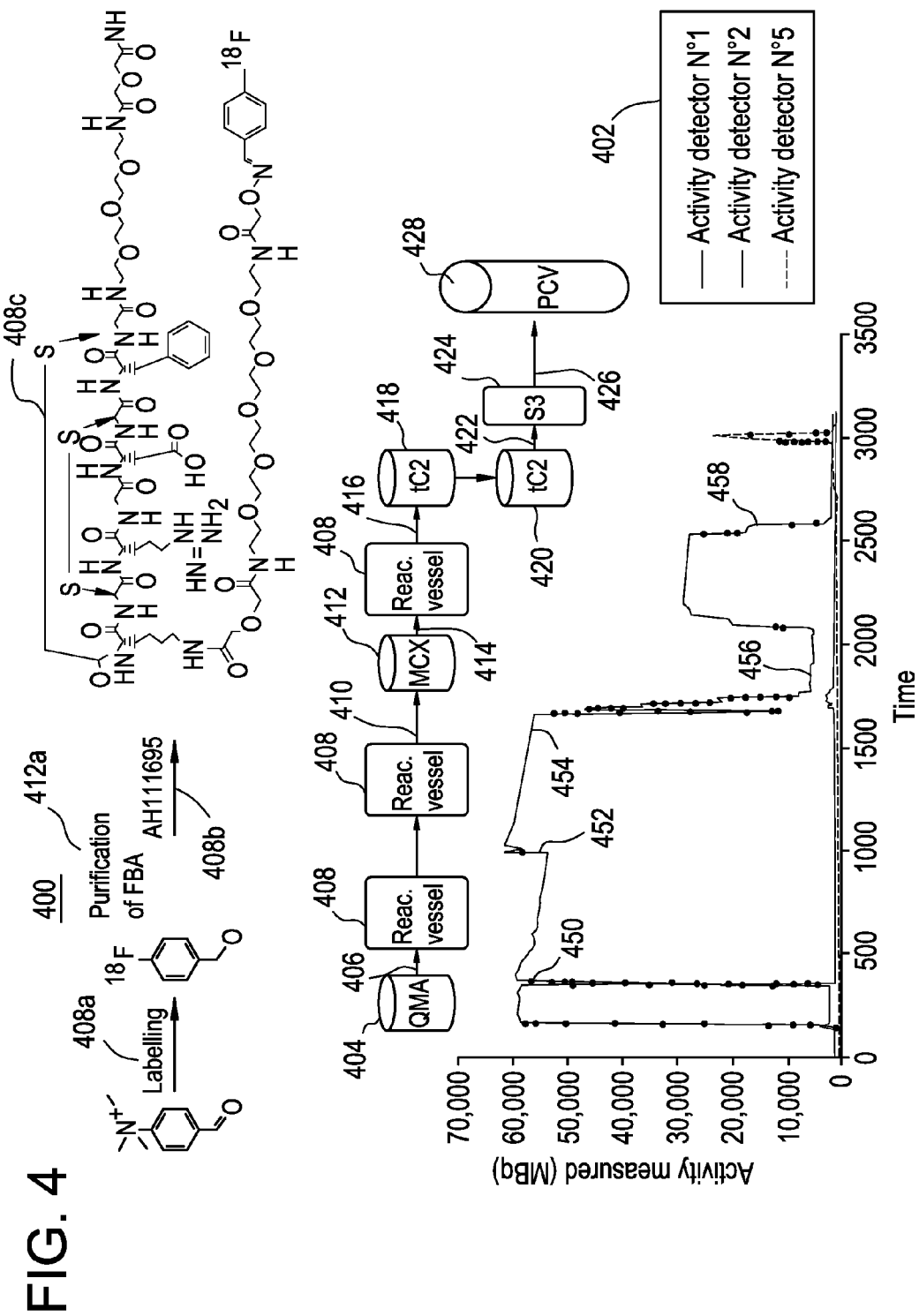
FIG. 4 depicts a plot of data collection file data with an overlay of synthesizer components according to an exemplary embodiment.

FIG. 4 depicts a plot 400 with an overlay of the components of the radiopharmaceutical synthesis process. As shown by the legend 402, the plot 400 is a plot of the activity at three different detectors. The plot 400 represents the same data as plotted in the plot 300 described above. The plots 300 and 400 depict the activity during the radiopharmaceutical synthesis process. Specifically, by way of non-limiting example, the plots 300 and 400 depict a data collection file obtained during the synthesis of Fluciclatide.

An exemplary radiopharmaceutical synthesis process is superimposed on the plot 400 as shown in FIG. 4. It should be appreciated that although this exemplary process is described in terms of production of Fluciclatide using $^{18}$F, the basics of the process and the components may be used in the production of other radiopharmaceuticals with appropriate modifications as understood in the art. The process begins with the purification of [$^{18}$F] obtained through, e.g., the nuclear reaction $^{18}$O(p,n)$^{18}$F by irradiation of a 95% $^{18}$-enriched water target with a 16.5 MeV proton beam in a cyclotron. The radioactivity is collected on a QMA cartridge 404 where $^{18}$F is trapped; impurities are removed; and the $^{18}$F is subsequently eluted at path 406 into a reaction vessel 408. In the reaction vessel 408, the $^{18}$F is first conditioned through a drying step to remove solvents including residual water, thus making the $^{18}$F more reactive. Next, at 408a, also in the reaction vessel 408, the 4-trimethylammonium benzaldehyde is labeled using the $^{18}$F, thereby replacing the 4-trimethylammonium moiety with a $^{18}$F. The resulting 4-[$^{18}$F]benzaldehyde (FBA) is transferred at path 410 to an MCX cartridge 412 for purification of FBA as shown at 412a. The FBA is transferred at path 414 back to the reaction vessel 408 and is conjugated at 408b with a Fluciclatide precursor AH111695 to form Fluciclatide as shown at 408c. This reaction is shown in detail in Scheme I, below.

Scheme I

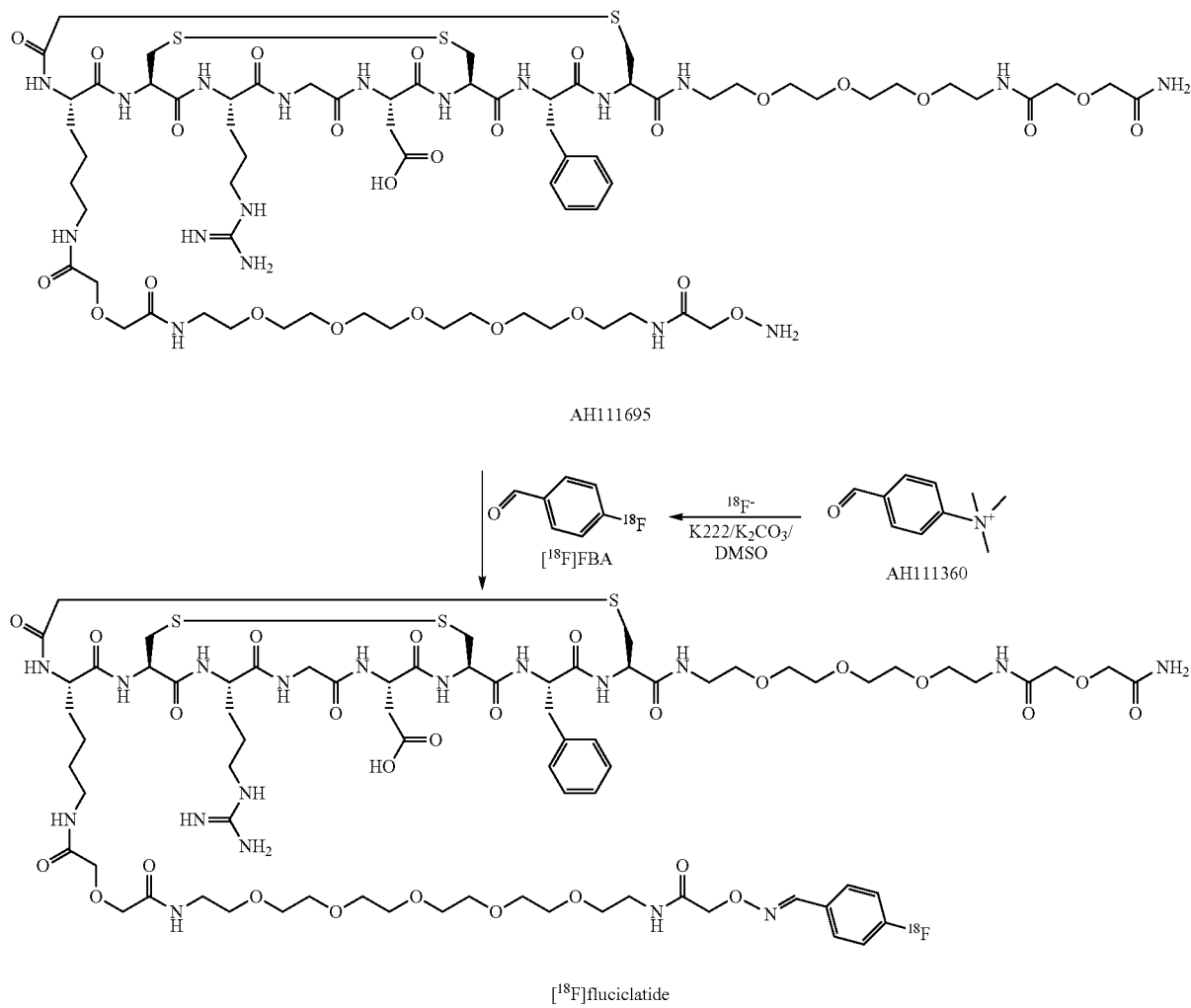

Next, using path 416, the Fluciclatide is transferred to and passed through the first of two SPE cartridges 418. The Fluciclatide obtained from the first SPE cartridge 418 subsequently migrates to a second SPE cartridge 420 for further purification (the SPE cartridges 418 and 420 may also be referred to as tC2 SPE cartridges). The Fluciclatide is transferred at 422 to a syringe 424 through which it is transferred at 426 into a production collection vial (PCV) 428. Although two SPE cartridges are shown in FIG. 4, the synthesizer may have one or more than two SPE cartridges and the SPE cartridges may be of different types and configurations.

According to exemplary embodiments, Activity Detector No. 1 is positioned in the vicinity of the QMA cartridge, Activity Detector No. 2 is positioned in the vicinity of the Reactor Vessel, and Activity Detector No. 5 is positioned in the vicinity of the outlet of the process that leads to a syringe or a production collection vial.

The elution of $^{18}$F off the QMA cartridge and into the reactor is illustrated by the sudden drop of the Activity Detector No. 1 trace and the rapid increase of the Activity Detector No. 2 trace at section 450 of the plot. The "jump" in the Activity Detector No. 2 trace after approximately 1000 sec (at section 452 of the plot) is caused by increased volume in the reactor when precursor is transferred into the reactor after evaporation of solvent. This jump occurs because activity is moved closer to the detector as the volume rises inside the reactor. During the labeling process, the volume remains constant and the slope of this plateau (at section 454 of the plot) illustrates the decay of the fluoride [$^{18}$F$^-$]. The activity detector is sensitive enough to even detect "splatter" inside the reactor when precursor is added. The purification of the FBA by the MCX cartridge is illustrated by the drop in the Activity Detector No. 2 trace followed by a lower plateau during the period the FBA is trapped inside the MCX cartridge, at section 456 of the plot. In other words, there is no detector located in proximity to the MCX cartridge. The trace increases again when activity is transferred back to the reactor. It should be appreciated that the elapsed time depicted refers to the start of the sequence, not the start of the overall synthesis. After starting a sequence, a synthesizer can be left idle for a period of time at a given step waiting for eventual delayed fluoride. A dialog box on the synthesizer may be need to be checked before proceeding. The start of sequence time is when this box is checked.

After the second synthetic step the Activity Detector No. 2 trace drops when product was transferred out to two SPE cartridges for final purification as shown in section 458 of the plot. When product is eluted off the SPE cartridge, and transferred to the production collection vial, it passes by Activity Detector No. 5.

Figure 5:
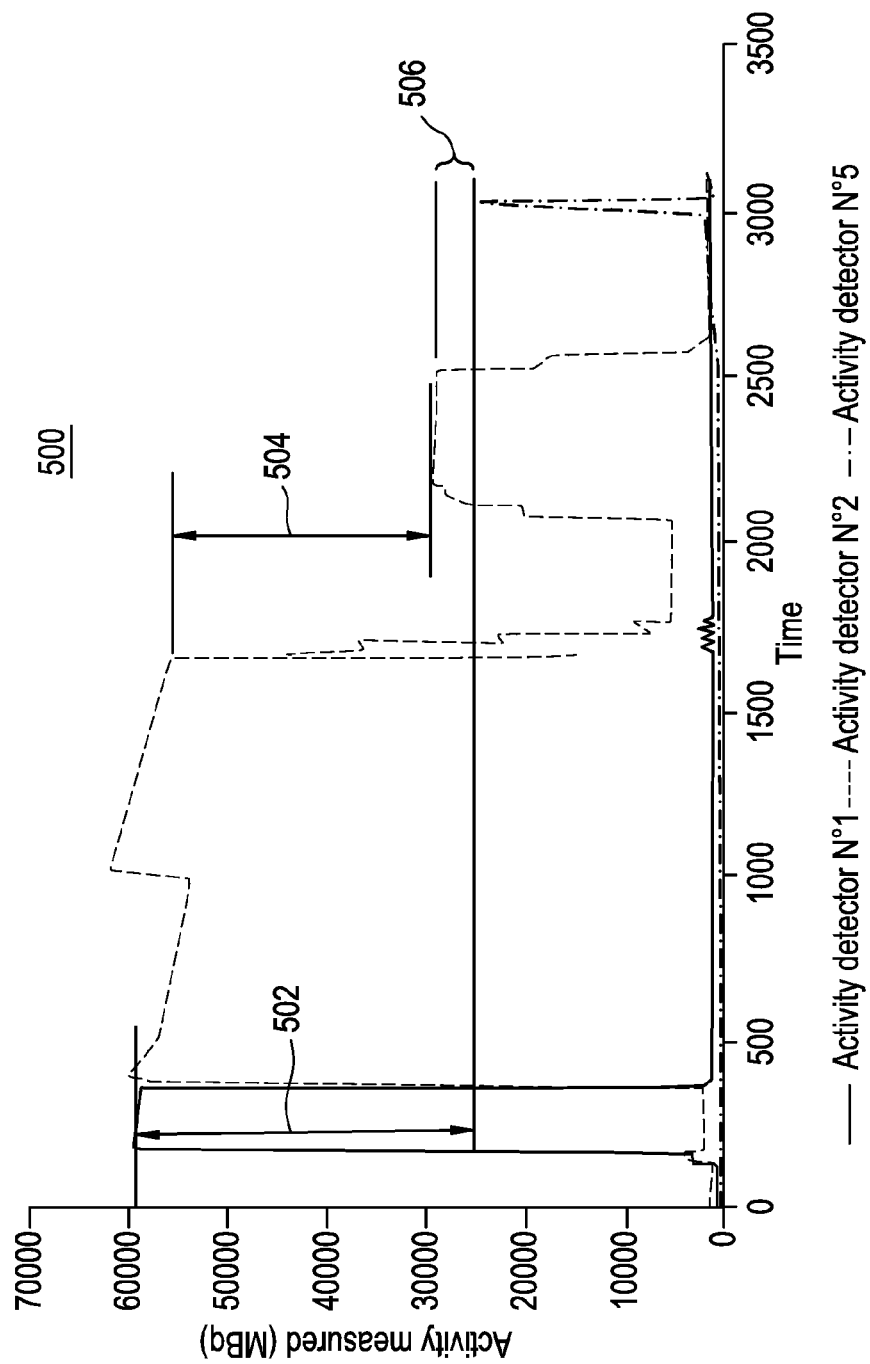
FIG. 5 depicts a plot of data collection file data showing the yield steps according to an exemplary embodiment.

FIG. 5 depicts a plot showing how certain information, specifically yield information, can be gleaned from the data collection file data according to an exemplary embodiment. Plot 500 depicts a plot similar to that of FIG. 4. The overall yield 502 is the sum of the first yield step 504 and the second yield step 506. These yield values can be used to assess the performance of the overall process, as well as identify problem areas of the process. According to exemplary embodiments, an exemplary or "standard" process with an exemplary yield may be determined for the system. The resulting data collected during the exemplary process, e.g., the measurements of the Activity Detectors, is plotted. The yield can be determined as shown in FIG. 5.

This resulting plot may form an exemplary "fingerprint" for the system. Subsequent runs made using the system can then be compared to this exemplary process. Deviations from the fingerprint can be noted through plots of the data collection file data as described above. From analysis of the plots in this comparison, problems with the system and its process may be readily identified and subsequently corrected. According to exemplary embodiments, if the trace shown in FIG. 3 is taken to be the fingerprint of a process that is optimal, a subsequent trace (e.g., from a subsequent synthesis run or from an instrument at a different site) can be compared to it. If the fingerprint of the subsequent trace varies significantly (e.g., more than 2%; more than 5%; more than 10% or more than 15%) in any region (e.g., the region that is covered by detectors 1, 2, 3, 4 or 5), the operator (or the synthesizer automatically) can diagnose the step of the synthesis that is not proceeding properly. According to exemplary embodiments, variations in the first yield step 504 and the second yield step 506 can be used to identify where in the process a problem may be occurring, either at the labeling step that forms [$^{18}$F]FBA; the conjugation step that forms [$^{18}$F]fluciclatide; or with any purification step involved in the synthesis process.

FIG. 6 depicts a set of yield predictions according to an exemplary embodiment. A table 600 represents data and yield predictions. The data is exemplary and non-limiting. According to exemplary embodiments, data is gathered from several synthesis runs on the same machine, as shown in column 602. Alternatively, or concurrently, these data can also be gathered from several locations or sites. These sites may be geographically separated and each site operates a radiopharmaceutical process on its synthesizer. The predicted yields, in this case from several runs on the same machine, are in column 604. The reported yields are in column 606. The predicted yields are calculated based upon the yields obtained from a plot, such as the plot 500.

It can be recognized that the yield data gleaned from the data collection file data agrees with the reported yield for the radiopharmaceutical. The reported yield is determined by a comparison of the first and second yields to the overall yield as shown in FIG. 5 above. The difference between these quantities is the percentage yield. It should be appreciated that the process can have several steps and actions and this is an exemplary comparison, as additional steps and actions may need to be taken into account for determining the overall yield. It is advantageous to be able to glean overall yield data from the data collection file of the synthesizer because such a determination may mean one less QC assessment that has to be performed on the sample, post-production prior to administering any of the produced radiopharmaceutical to a patient, thus saving time and resources.

In addition to yield data one can also glean purity data from the data collection file. One of the detectors not shown in FIGS. 4 and 5 is Activity Detector No. 4. This detector is located in the vicinity of the two SPE cartridges, as SPE cartridges 418 and 420 depicted in FIG. 4. While, the data from this detector is not shown in FIGS. 4 and 5, it is nevertheless collected during the synthesis run. When this data is plotted the traces shown in FIGS. 7A and 7B may be obtained. It should be understood that these traces are exemplary only.

FIGS. 7A and 7B depict traces 702 and 704, respectively, of activity from Activity Detector No. 4 for a portion of the synthesis reaction. Both figures contain plots of multiple traces from different runs. For example, FIG. 7A depicts traces from multiple runs at a particular site as indicated by the legend 702. FIG. 7B shows three different traces obtained while the SPE cartridges were kept at three different temperatures, as shown by the legend 704. From these traces, it can be observed that the changes in activity measured from the highest, or maximum, activity read by Activity Detector No. 4 and the minimum activity read by the detector can be correlated to the level of impurities present in the radiopharmaceutical produced in any given synthesis run (referring to the right hand portion of the traces, shown by section 706 of the traces). For example, in FIG. 7A, the smaller the change in activity between the maximum value of any given trace, such as section 710, and the minimum value for any given trace, such as section 712, is correlated to high levels of impurities. In contrast, the larger the change in activity between the maximum value of any given trace, such as section 714, and the minimum value for any given trace, such as section 716, is correlated with lower levels of impurities.

FIG. 7B also depicts this behavior, in this case of the synthesis of the radiopharmaceutical anti-1-amino-3-[$^{18}$F]fluorocyclobutane-1-carboxylic acid, otherwise known as FACBC. The trace 720, which depicts activity at 27° C., has total impurities of 106 µg/mL. The trace 722, which depicts activity at 30° C., has total impurities of 56 µg/mL, while the trace 724, which depicts activity at 28° C., has total impurities of 79 µg/mL. The trace behavior depicts these impurity levels. From FIG. 7B, it can be seen that the distance from the point 730 of the trace 720 to its lowest value 732, it much less than either of the similar points of the traces 722 and 724 (such as, for example, the distance from the point 734 on the trace 722 and the lowest value 736 is greater than that of trace 720. A similar analysis may be performed for the trace 724 (with the highest point and lowest point being labeled as 738 and 740, respectively). A specific portion of the trace at a specific time may be designated for the measurement of the high and low points to ensure consistency among readings for different traces.

From the data collection file one can also glean data regarding how effective certain processes are during the synthesis run. FIG. 8 depicts a plot 800 of a series of traces depicting a portion of runs shown activity at Activity Detector No. 5 during the final SPE purification step at a particular site. The plot 800 is exemplary and non-limiting. A legend 802 is provided. A table 804 provides a summary of the run number vs. SPE recovery % vs. reported yield percentage.

The behavior of the traces shown in the plot 800 can be analyzed and conclusions drawn therefrom. For example, focusing on the trace and data corresponding to run J181 (labeled by 806 in the legend 802 and the table 804), certain behavior can be seen. For example, the large delta between the SPE Recovery % and the Reported Yield % is usually indicative of a problem in the synthesis process, specifically the labeling step (e.g., the step yielding [$^{18}$F]FBA, when the radiopharmaceutical in question is [$^{18}$F]fluciclatide). In the case of run J181, in the synthesis of [$^{18}$F]fluciclatide, such a large delta is indicative of a problem in the labeling step yielding [$^{18}$F]FBA. It should be appreciated that in practice every step and action are monitored and abnormal indications can be detected. For example, untypical syringe movement can be detected through the data collection files. The activity detectors are capable of catching the consequence or result of a particular step or action during the synthesis process. Hence, it can be see if the action, e.g., an atypical syringe movement, affected the outcome the production.

Data corresponding to this run can be seen in FIG. 6 at 610 also. The data 610 shows that the run has a low fluorination in the step of 45% (depicted in the Yield Labeling column of table 600). Based on this, the trace 808 corresponding to this run in FIG. 8 behaves in a certain manner. For example, the trace 808 has a higher activity than the other runs in the latter part of FIG. 800. By noting behavior of this sort, insightful observations can be made into a particular synthesis process and what is happening at each step. This and other observations can be made from an analysis of the data and the traces therefrom.

Figure 9A:
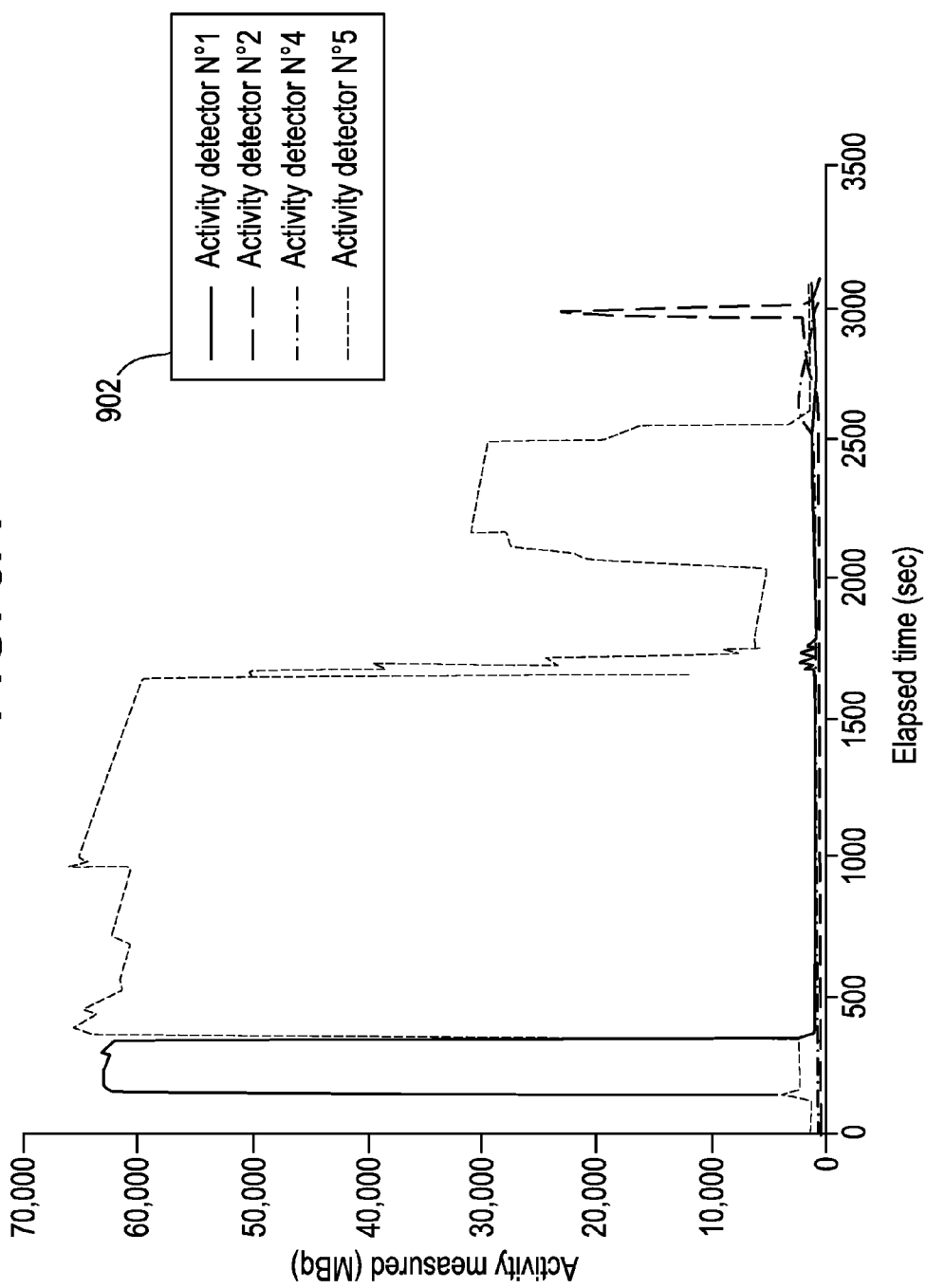
Figure 9C:
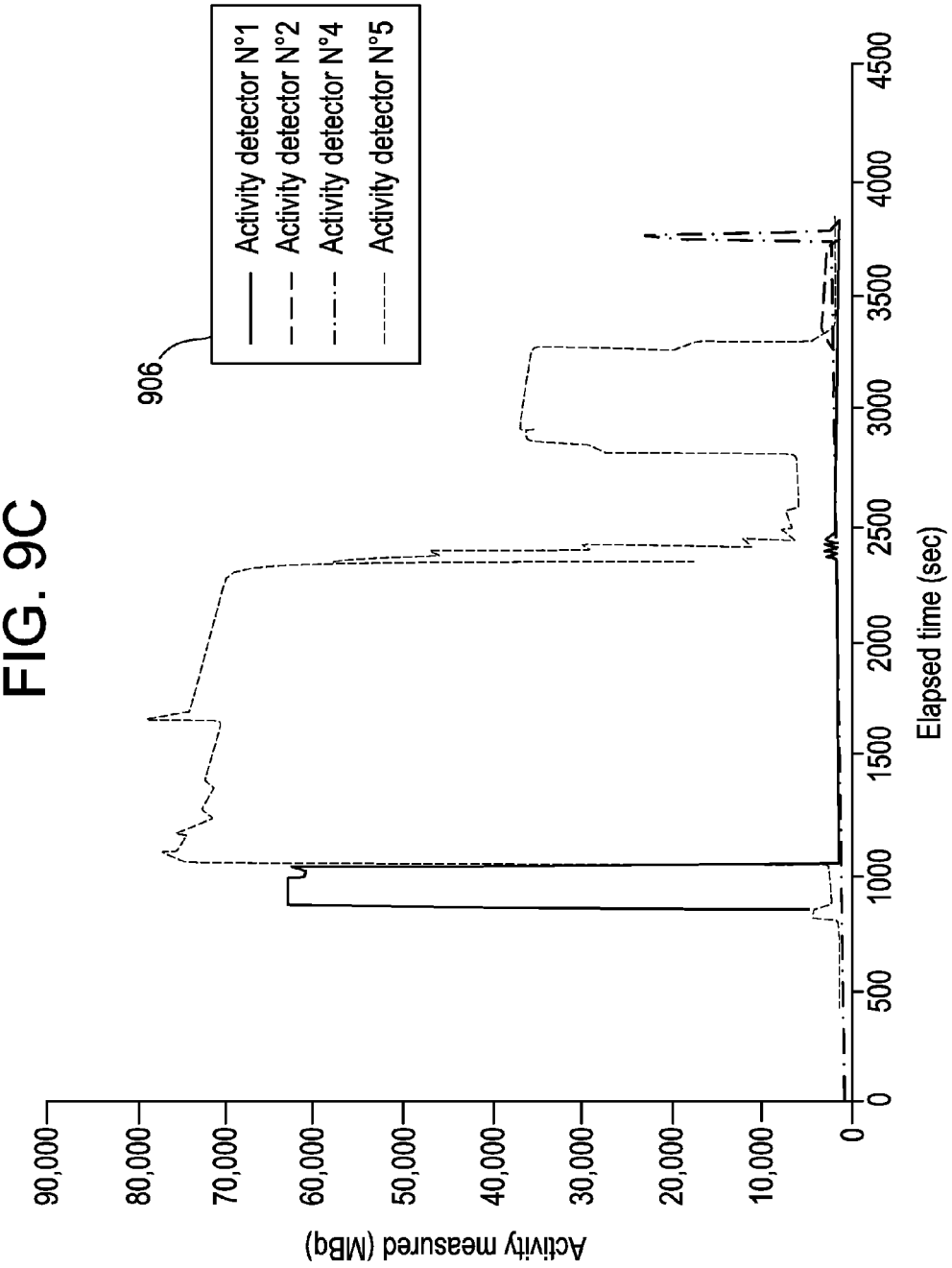

FIGS. 9A-C each depict an activity plots or traces from three different production sites based on data collection file data. By way of non-limiting example, FIG. 9A represent a production run at a site in Norway, FIG. 9B represents a production run at a site in Sweden, and FIG. 9C represents a production run at a site in the UK. Each run is a Fluciclatide production run using a synthesizer which, by way of non-limiting example, are FASTlab systems here. As can be seen in each Figure, data corresponding to Activity Detectors Nos. 1, 2, 4, and 5 are plotted for each. Legends 902, 904, and 906 on each FIG. 9A-C, respectively, provide reference to the traces for each Activity Detector. As can be seen, each plot is similar in structure and shape to that shown in FIGS. 3 and 4 described above, as these plots were obtained using the same equipment and process as depicted in those Figures.

When comparing FIGS. 9A-C, it can be seen that there are differences in the relative peak heights; e.g., between the readings of Activity Detector No. 1 (QMA) and Activity Detector No. 2 (reactor) between the different production sites and their specific synthesizers. In an ideal case, the readings of Activity Detectors Nos. 1 and 2 should be almost equal since the amount of activity entering reactor after elution of the QMA is supposed to be almost the same since the recovery activity from the QMA is >99%. The same variations are also seen between Activity Detectors Nos. 2 and 5. The differences between Activity Detectors Nos. 2 and 5 are used for the overall yield predictions (as described above). Hence, inaccuracy of these two detectors effects the accuracy of yield prediction. In data given in FIG. 6 (which represents data corresponding to FIG. 9A), correlation between estimated and reported yields is observed. However, when the same estimations are done on other synthesizers, e.g., FIGS. 9B and 9C, the effect of variations between Activity Detectors Nos. 2 and 5 are seen. FIG. 10 includes this data. FIG. 10 depicts a data table corresponding to the plots of FIGS. 9A-C. The data 1002 labeled as "NMS" corresponds to FIG. 9A; the data 1004 labeled as "UI" corresponds to FIG. 9B; and the data 1006 labeled as "TGC" corresponds to FIG. 9C. The differences in yield data may be attributed to the differences in the Activity Detector measurements.

As seen in FIG. 10, the accuracy of the yield prediction varies between sites and particular synthesizers. In order to use the data for analysis of the synthesizer production for troubleshooting or other investigations, the data from the data collection files, e.g., log files, (as described above) are extracted from the synthesizer and analyzed. Plots, such as those in FIGS. 9A-C are created. However, since there are variations amongst synthesizers, even at the same site, the data analysis may be not be directly comparable. Activity trending may be a useful tool for monitoring reaction performance.

A method of correcting activity detector measurements is described. A basic synthesizer sequence where a known amount of activity is passed in vicinity of the different Activity Detectors. This is accomplished by mating a cassette with the synthesizer (as would be done if a production run was being made. The cassette may be specifically configured cassette to support the required measurements or a production cassette may be used, possibly with modifications. No chemical reactions are required. The operations required are trapping and elution of the QMA cartridge with an accurately known volume followed by movement of the eluted 18F-fluoride solution around the cassette using syringe movements and gas pressure. A correlation factor for each detector can then be calculated as shown in the following example.

When activity arrives from the cyclotron, the activity is accurately measured in an ion chamber. For illustration purposes, the net activity transferred on to the synthesizer in this example is 100 GBq. In the synthesizer, Activity Detector No. 1 reads 80 GBq, Activity Detector No. 2 reads 110 GBq, and Activity Detector No. 5 reads 90 GBq. The readings are then adjusted for decay. For simplification of the present example, the decay correction is not included. Based on the readings, the correlation factors for this particular synthesizer would then be:

Correlation factor for Activity Detector No. 1: 100/80=1.25

Correlation factor for Activity Detector No. 2: 100/110=0.91

Correlation factor for Activity Detector No. 5: 100/90=1.11

Data for the other detectors including any custom placed additional detectors can of course be obtained in the same manner and correlation factors can be calculated. The correlation factors can then be used during the data analysis of the data collection file. This methodology does not require a modification to the synthesizer system's programming although it is contemplated that the programming may be modified so that the correlation factors are automatically determined and applied. It should be appreciated that calculation could be a part of a PET tracer manufacturing set-up since the detector check is straightforward. This operation could be repeated on regular basis to see if detectors need to be calibrated. This operation can be repeated with different activities for control of the radio detector linearity. Additionally, this operation can be carried out across multiple sites and, by using the correlation factors, activity detector readings can be compared across these multiple sites. It should further be appreciated that additional correlation factors can be calculated to compare data from synthesizers to other baselines or standards.

FIG. 11 depicts an activity plot or trace for an automated synthesizer at a production site after calibration of the synthesizer's detectors. It can be seen that the relative peak heights; e.g., between the readings of Activity Detector No. 1 (QMA) and Activity Detector No. 2 (reactor) give detector readings after calibration that are consistent with activity transfer through the synthesis process. The reading from Activity Detector No. 1 is higher than the reading for Activity Detector No. 2 showing both radioactive decay and losses of activity as the synthesis process is performed. This correct relative calibration of the detectors allows more precise yield calculations or other inferences based on the activity detector readings.

While the foregoing description includes details and specific examples, it is to be understood that these have been included for purposes of explanation only, and are not to be interpreted as limitations of the present invention.

While the embodiments have been particularly shown and described above, it will be appreciated that variations and modifications may be effected by a person of ordinary skill in the art without departing from the scope of the invention. Furthermore, one of ordinary skill in the art will recognize that such processes and systems do not need to be restricted to the specific embodiments described herein. Other embodiments, combinations of the present embodiments, and uses and advantages of the present invention will be apparent to those skilled in the art from consideration of the specification and practice of the invention disclosed herein. The specification and examples should be considered exemplary.

What is claimed is:

1. A method of performing radiosynthesis with an automated radiosynthesizer, the radiosynthesizer having a plurality of individual activity detectors operably associated therewith, comprising the steps of:
   Providing a calibration standard comprising a source of gamma radiation having both a known activity and a known time decay correlation factor in the vicinity of each activity detector of the radiosynthesizer at defined time intervals;
   Measuring activity data with each activity detector as said calibration standard is in the vicinity thereof;
   Determining the correlation factor $C_f$ for each individual activity detector as $$C_f = (x/y) * z$$

where x is the known activity of said calibration standard, y is the activity data measured at the each individual activity detector, and z is a defined decay by time decay correlation factor for said calibration standard;
   Normalizing each individual activity detector prior to the radiosynthesis; and
   Synthesizing a tracer with the radiosynthesizer, wherein the synthesizing step further comprises the step of:
   detecting activity readings by each individual activity detector as the tracer is synthesized, and
   monitoring the radiosynthesis by applying the correlation factor $C_f$ determined for said each individual activity detector to the detected activity readings.

2. The method of claim 1, wherein said source of gamma radiation is a positron-emitting isotope.

3. The method of claim 1, further comprising the step of building a data collection file comprising a set of data recorded at one second intervals at each activity detector during a radiopharmaceutical synthesis.

4. The method of claim 1, wherein the step of determining the correlation factors $C_f$ for each activity detector is performed automatically.

5. The method of claim 1, wherein the step of applying the correlation factor is performed automatically by a computer controlling the synthesizer.

6. The method of claim 5, wherein the computer is on board the synthesizer.

7. The method of claim 1, wherein the step of providing the calibration standard further comprises the step of connecting a cassette to the synthesizer, said cassette including valves and conduits for conducting the calibration standard therethrough to each activity detector, wherein said cassette is operable by the radiosynthesizer.

8. The method of claim 1, wherein said calibration standard is directed to a QMA cartridge in the vicinity of a first activity detector of the synthesizer.

9. The method of claim 1, wherein the synthesizer includes between two and five activity detectors.

10. The method of claim 1, further comprising: optimizing a production run of the radiosynthesizer by normalizing data collected from the production run to account for variations at the different manufacturing or synthesis sites.

11. A non-transitory computer readable storage medium comprising computer readable program code including instructions for determining a correlation factor of each of a plurality of individual activity detectors on a radiosynthesizer, wherein execution of the computer readable program code causes a processor to carry out the determining step of claim 1,
   wherein the determined correlation factor is to be applied to normalize each of the plurality of activity detectors during synthesis of a tracer with the radiosynthesizer.

12. The non-transitory computer-readable storage medium of claim 11, further comprising computer readable program code including instructions for applying the correlation factor determined for each activity detector on the radiosynthesizer.

13. A method of calibrating an automated radiosynthesizer, the radiosynthesizer having a plurality of individual activity detectors operably associated therewith, comprising the steps of:
   Providing a calibration standard comprising a source of gamma radiation having both a known activity and a known time decay correlation factor in the vicinity of each activity detector of the radiosynthesizer at defined time intervals;
   Recording activity data from each activity detector as said calibration standard is in the vicinity thereof;
   Determining the correlation factor $C_f$ for each individual activity detector as $$C_f = (x/y) * z$$

wherein x is the known activity of said calibration standard, y is the activity data recorded at the particular individual activity detector, and z is a defined decay by time decay correlation factor for said calibration standard, and
   wherein the determined correlation factor is to be applied to normalize each individual activity detector during synthesis of a tracer with the radiosynthesizer.

14. The method of claim 13, wherein said gamma source is a positron-emitting isotope.

15. The method of claim 14, wherein said applying step is performed automatically by a computer controlling the synthesizer.

16. The method of claim 13, further comprising the step of applying the correlation factor to activity readings by each individual activity detector recorded during a synthesis operation in which a tracer is synthesized.

17. The method of claim 13, further comprising the step of building a data collection file comprising a set of data recorded at one second intervals at each activity detector during a radiopharmaceutical synthesis.

18. The method of claim 13, wherein the step of providing the calibration standard further comprises the step of connecting a cassette to the synthesizer, said cassette including valves and conduits for conducting the calibration standard therethrough to each activity detector, wherein said cassette is operable by the radiosynthesizer.

19. The method of claim 13, wherein said calibration standard is directed to a QMA cartridge in the vicinity of a first activity detector of the synthesizer.

20. A non-transitory computer readable storage medium comprising computer readable program code including instructions for determining a correlation factor of each of a plurality of individual activity detectors on a radiosynthesizer, wherein execution of the computer readable program code causes a processor to carry out the determining step of claim 13.

* * * * *